(12) United States Patent
Horton et al.

(10) Patent No.: US 7,554,339 B2
(45) Date of Patent: Jun. 30, 2009

(54) ELECTROMAGNETIC TESTING OF AN ENCLOSURE OR CAVITY USING A DISCRETE FREQUENCY STIR METHOD

(75) Inventors: Nathaniel T. Horton, Burien, WA (US); Dennis M. Lewis, Lynnwood, WA (US)

(73) Assignee: The Boeing Company, Chiacgo, IL (US)

( * ) Notice: Subject to any disclaimer, the term of this patent is extended or adjusted under 35 U.S.C. 154(b) by 146 days.

(21) Appl. No.: 11/566,050

(22) Filed: Dec. 1, 2006

(65) Prior Publication Data

US 2008/0127756 A1      Jun. 5, 2008

(51) Int. Cl.
*G01R 27/28*      (2006.01)
(52) U.S. Cl. .................. 324/627; 324/636; 324/637
(58) Field of Classification Search .............. 324/627, 324/636, 637
See application file for complete search history.

(56) References Cited

U.S. PATENT DOCUMENTS

| | | | | |
|---|---|---|---|---|
| 4,472,784 A | * | 9/1984 | Blachman ................. | 702/83 |
| 5,153,524 A | * | 10/1992 | McCormack .............. | 324/627 |
| 5,327,091 A | * | 7/1994 | Loughry .................. | 324/627 |
| 5,530,412 A | * | 6/1996 | Goldblum ................ | 333/232 |
| 6,052,420 A | * | 4/2000 | Yeap et al. ............... | 375/346 |
| 6,255,830 B1 | * | 7/2001 | Rollin et al. ............. | 324/627 |
| 6,265,466 B1 | * | 7/2001 | Glatkowski et al. ...... | 523/137 |
| 6,295,032 B1 | * | 9/2001 | Podgorski ................ | 343/703 |
| 6,563,327 B1 | * | 5/2003 | Leferink .................. | 324/637 |
| 6,795,030 B2 | * | 9/2004 | Klingler et al. .......... | 343/703 |
| 6,885,265 B2 | * | 4/2005 | Li et al. .................. | 333/227 |
| 7,347,101 B2 | * | 3/2008 | Thomson et al. ......... | 73/773 |

OTHER PUBLICATIONS

Arnaut, Luk, On the maximum rate of fluctuation in mode-stirred reverberation, IEEE Trans. on Elec. Comp., V. 47, No. 4, Nov. 2005, p. 781-804.*

NIST Technical Note 1375, "Band-Limited, White Gaussian Noise Excitation for Reverberation Chambers and Applications to Radiated Susceptibility Testing," dated Jan. 1996.

(Continued)

*Primary Examiner*—Timothy J. Dole
*Assistant Examiner*—Thomas F. Valone
(74) *Attorney, Agent, or Firm*—Ostrager Chong Flaherty & Broitman P.C.

(57) ABSTRACT

The "discrete frequency stir" (DFS) method provides improved mode stir testing of electromagnetic characteristics of an enclosure/cavity. Adequate sampling of the electric field inside the enclosure/cavity is provided by electronic perturbation or "stirring" of the field with a short duration, continuous wave, radiated source where the wave frequency is stepped in small steps across a frequency range of interest. The frequency steps are selected to be at least slightly larger than the resonant mode bandwidth associated with the given enclosure/cavity in order to provide statistically independent measurements. A stirring bandwidth is selected to encompass a statistically significant number of these measurement samples while maintaining adequate frequency resolution. A statistical evaluation of the measured field is then performed over this stirring bandwidth. For example, the average field level at a given frequency is determined by averaging over the samples contained within the stirring bandwidth when centered on that frequency.

20 Claims, 14 Drawing Sheets

OTHER PUBLICATIONS

L. Scott, "Mode-Stir Measurement techniques for EMC Theory & Operation," IEE Colloquium on Antenna Measurements, Jun. 19, 1998, pp. 8/1 - 8/7.

D. A. Hill, "Reciprocity in Reverberation Chamber Measurments," IEEE Trans. on Electromagnetic Compatibility, vol. 45, No. 1, Feb. 2003.

M. O. Hatfield, "Shielding Effectiveness Measurments Using Mode-Stirred Chambers: A Comparison of Two Approaches," IEEE Trans. on Electromagnetic Compatibility, vol. 30, No. 3, Aug. 1988.

Corona et al, "Reverberation Chambers as Sources of Stochastic Electromagnetic Fields," IEEE trans. on Electromagnetic Compatibility, vol. 38, No. 3, Aug. 1996.

Freyer et al, "Comparison of Measured and Theroretical Statistical Parameters of Comples Cavities," IEEE International Symposium on EMC, Aug 19-23, 1996, pp. 250-253.

J. G. Kostas and B. Boverie, "Statistical Model for a Mode-Stirred Chamber," IEEE Trans. EMC, vol. EMC-33, No. 4, pp. 366-370, Nov. 1991.

Loughry, Thomas A., "Frequency Stirring: An Alternate Approach to Mechanical Mode-Stirring for the Conduct of Electromagnetic Susceptibility Testing," Philips Laboratory, Kirtland Air Force Base, NM, dated Nov. 1991.

A. K. Mitra and T. F. Trost, "Statistical Simulations and Measurements Inside a Microwave Reverberation Chamber," IEEE 1997 International Symposium on EMC, Aug. 18-22, 1997, pp. 48-53.

D. I. Wu and D. C. Chang, "The Effect of on Electrically Large Stirrer in a Mode-Stirred Chamber," IEEE Trans. on Electromagnectic Compatability, vol. 31, No. 2, May 1989.

A. K. Mitra and T. F. Trost, " Power Transfer Characteristics of a Microwave Reverberation Chamber," IEEE Trans. on Electromegnetic Compatibility, vol. 38, No. May 1996.

* cited by examiner

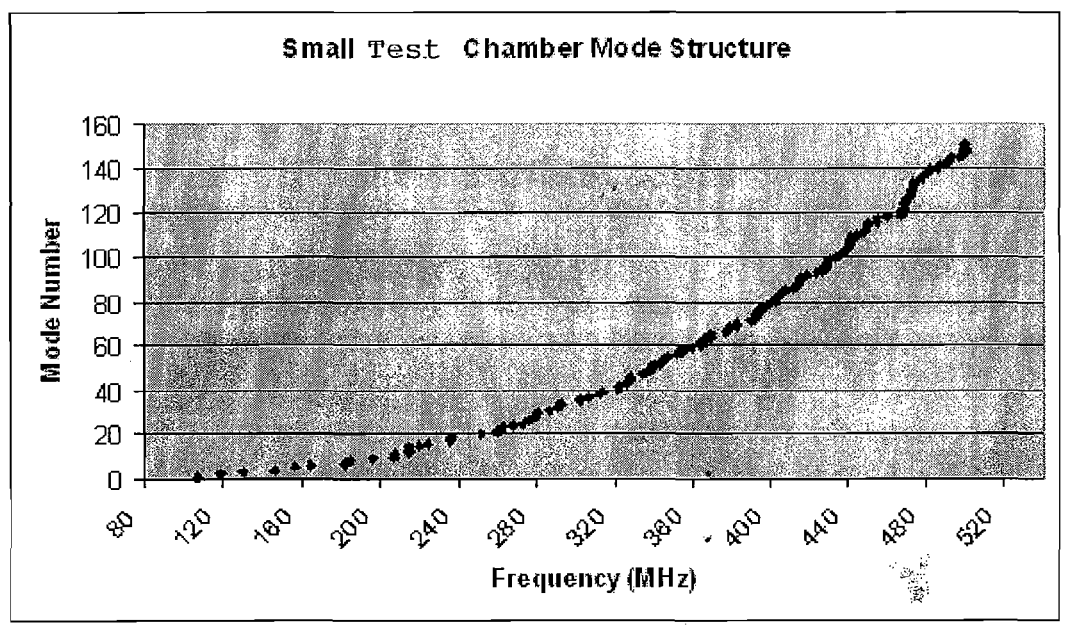
Figure 1. First 150 resonant modes in a small sample chamber.
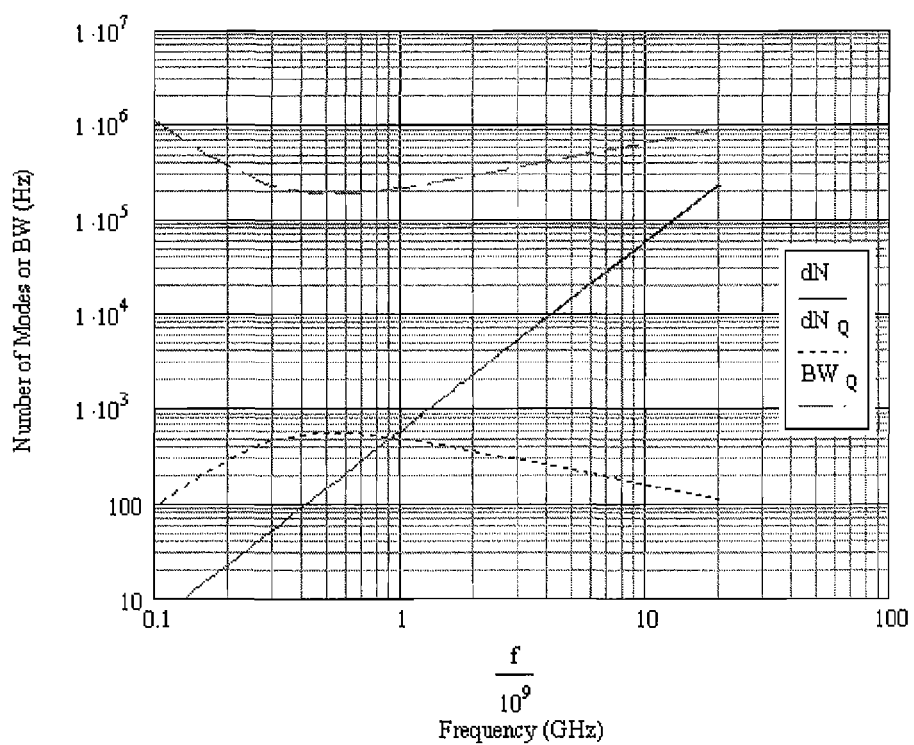
Figure 2. Mode density, reduced number of modes, and resonant mode bandwidth.

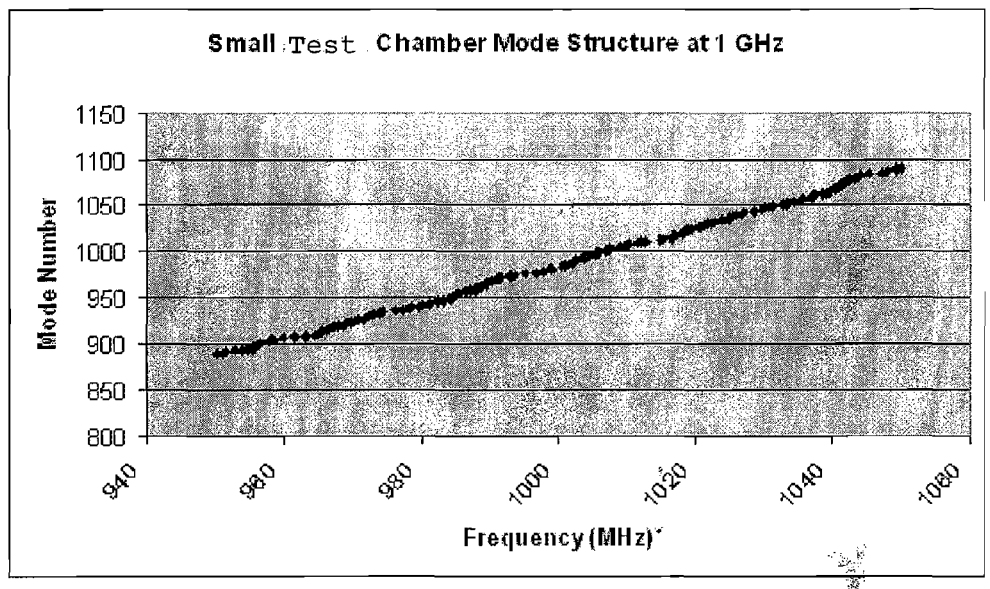
Figure 3. Modes existing within a 100 MHz bandwidth centered at 1 GHz.
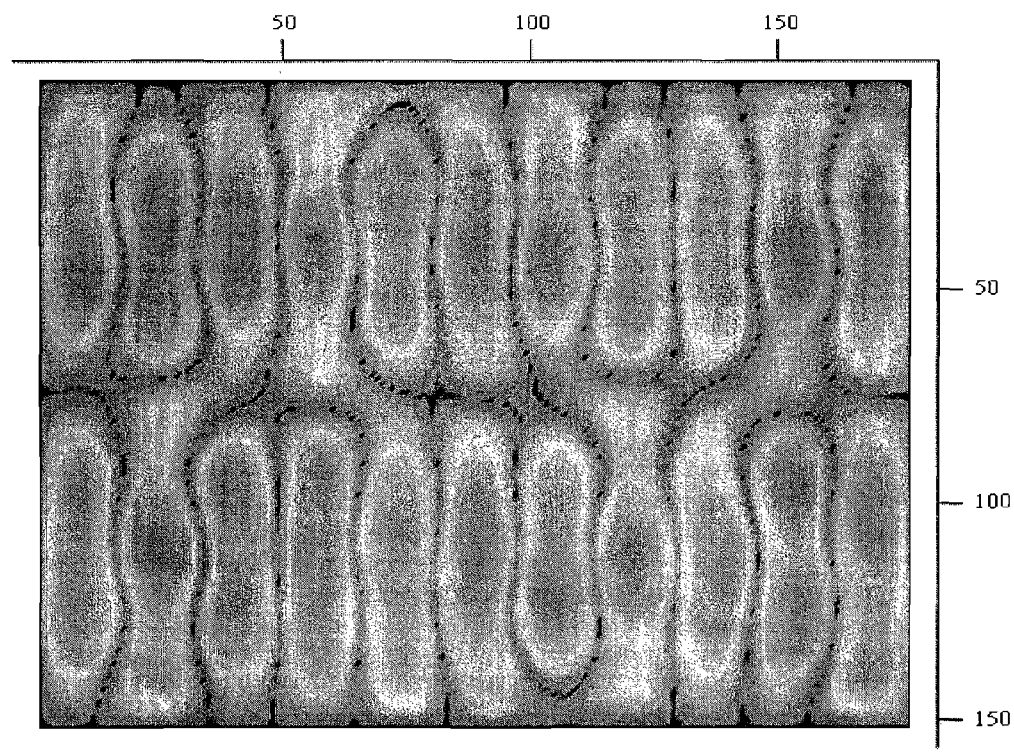
Figure 4. Horizontal cross-section of $TM_{11,2,0}$ in the small sample chamber.

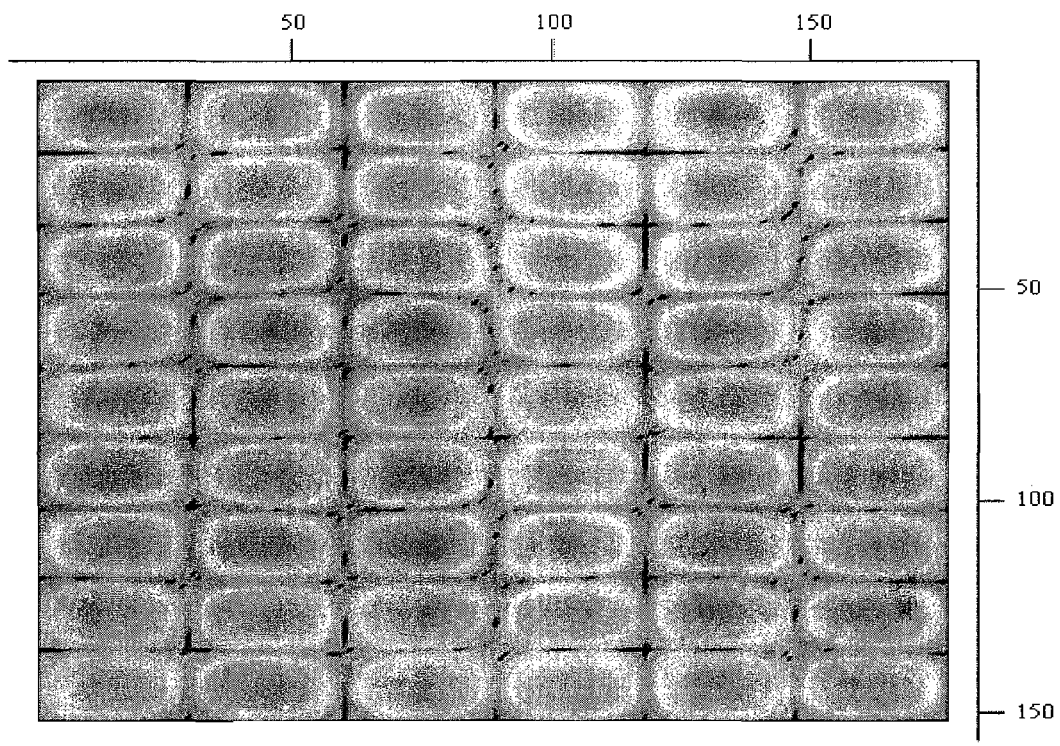
Figure 5. Horizontal cross-section of $TM_{6,9,0}$ in the small sample chamber.

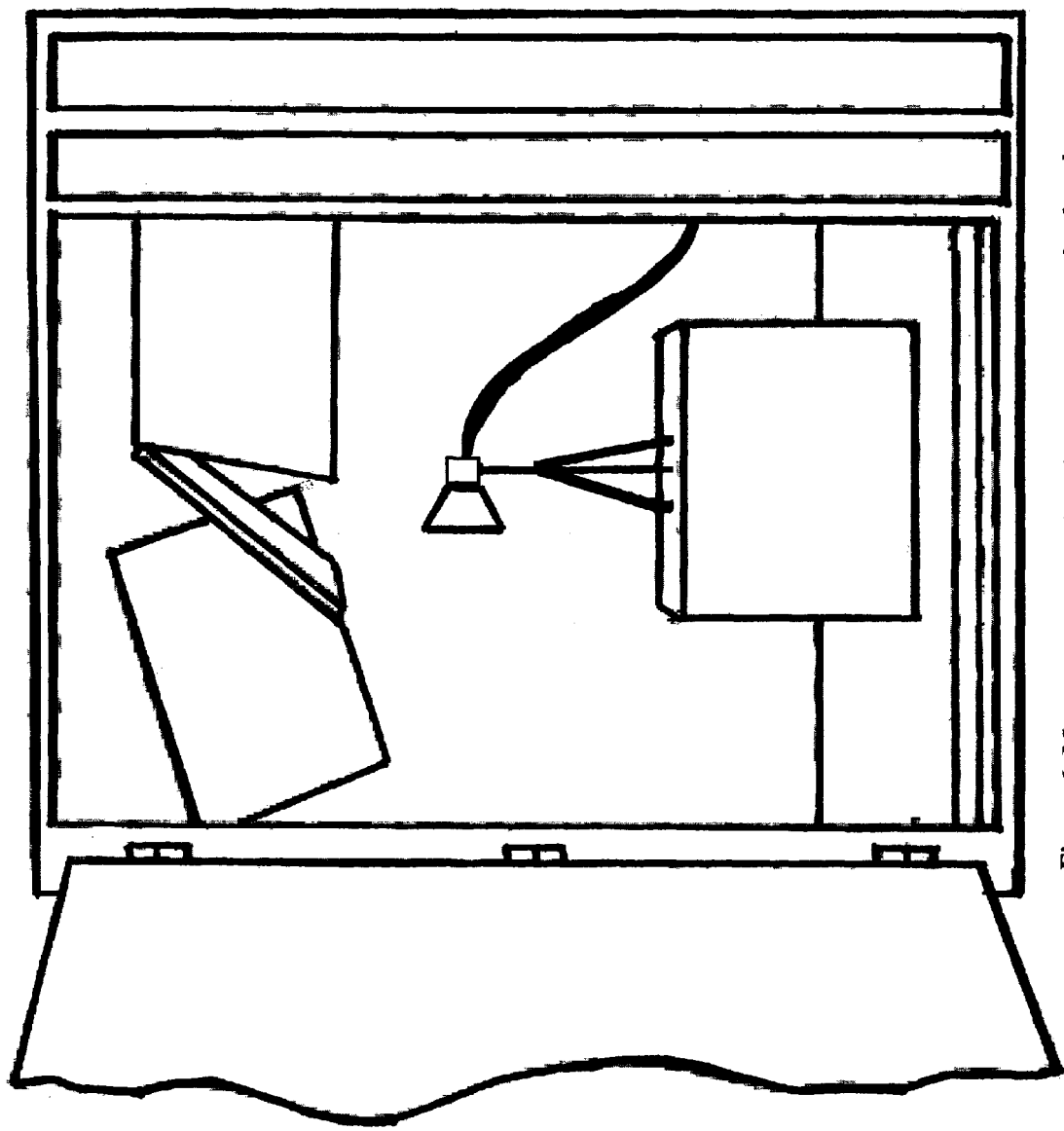
Figure 6. Measurement locations in the small sample chamber.

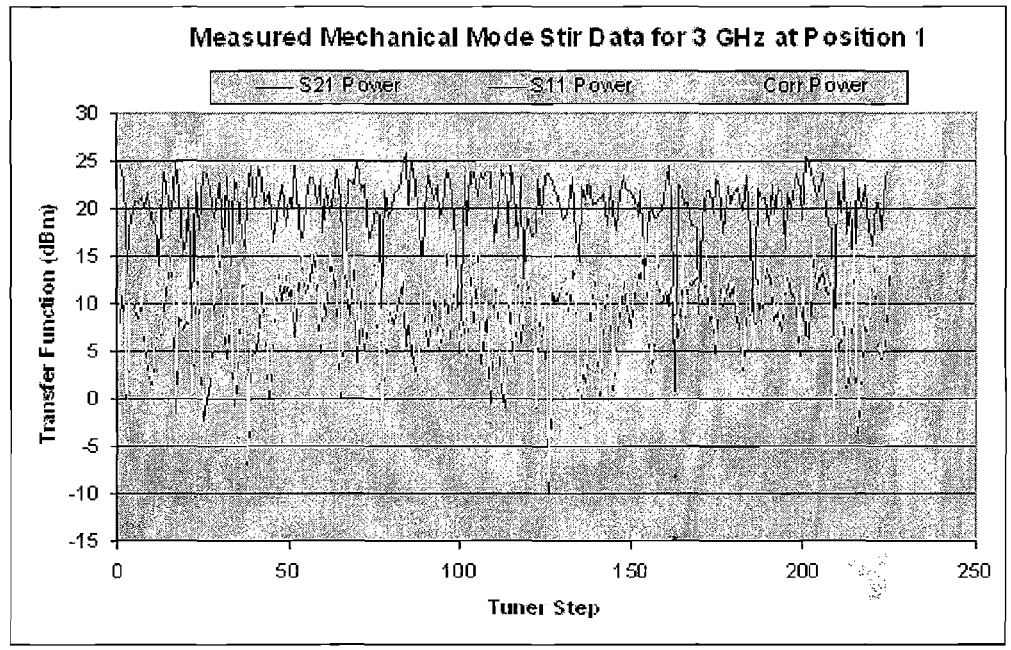
Figure 7. MS measured data for 3 GHz at position 1.
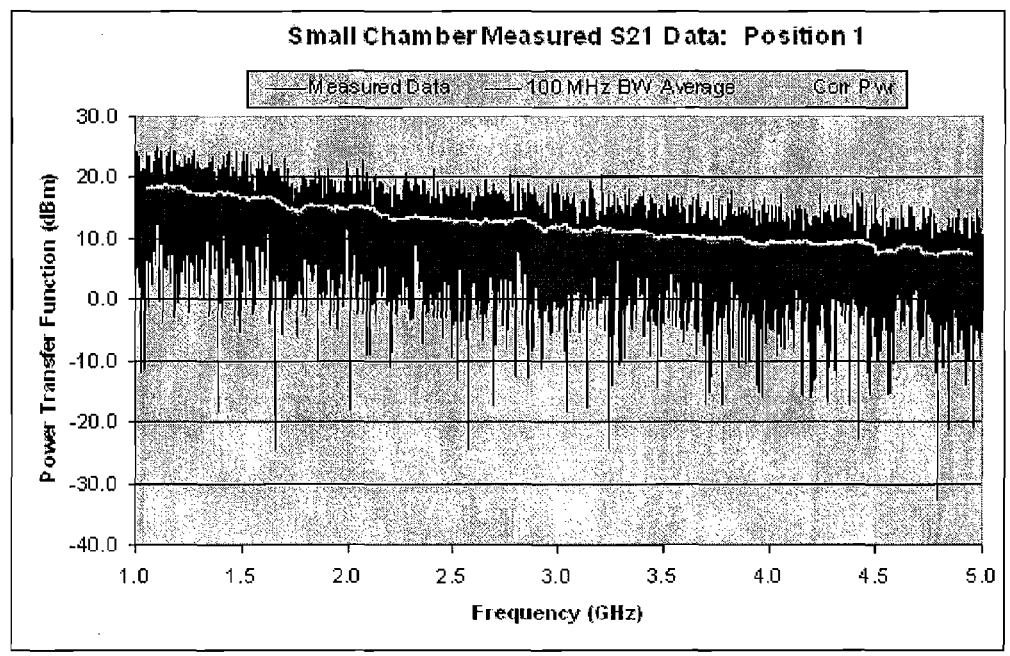
Figure 8. DFS measured data for 1-4.5 GHz at position 1.

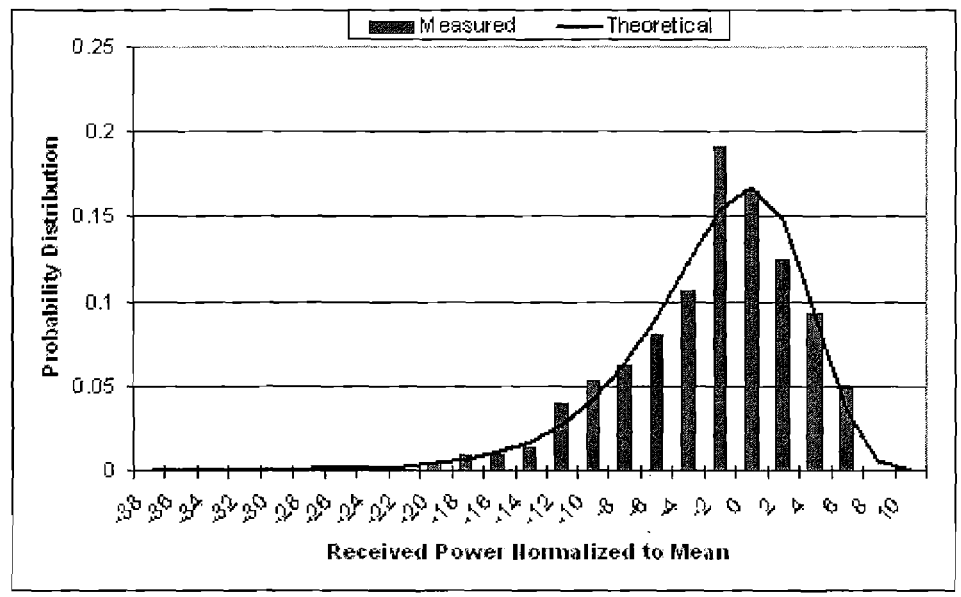
Figure 9. Chi-square distribution of MS data for 1 GHz at position 1.
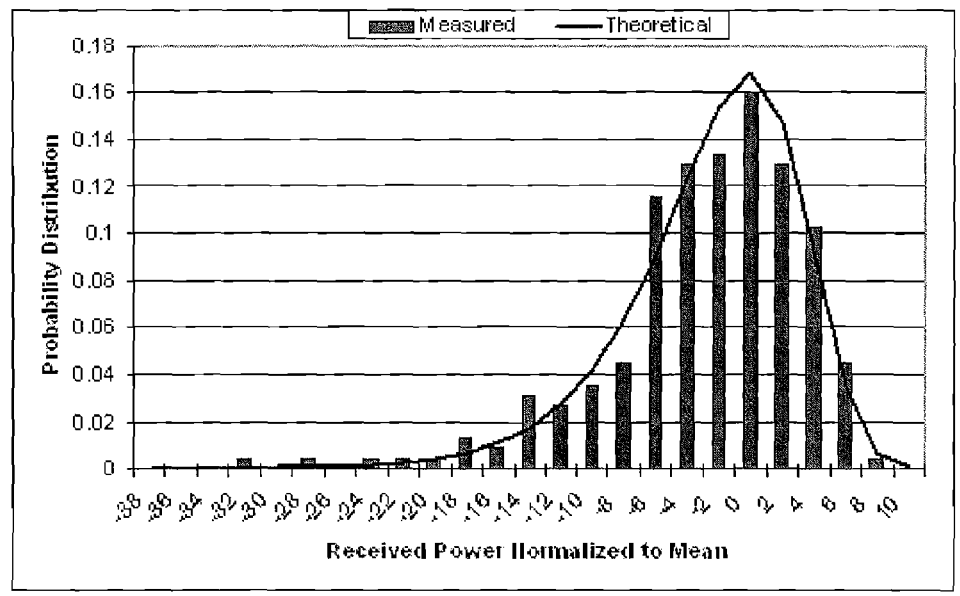
Figure 10. Chi-square distribution of MS data for 10 GHz at position 1.

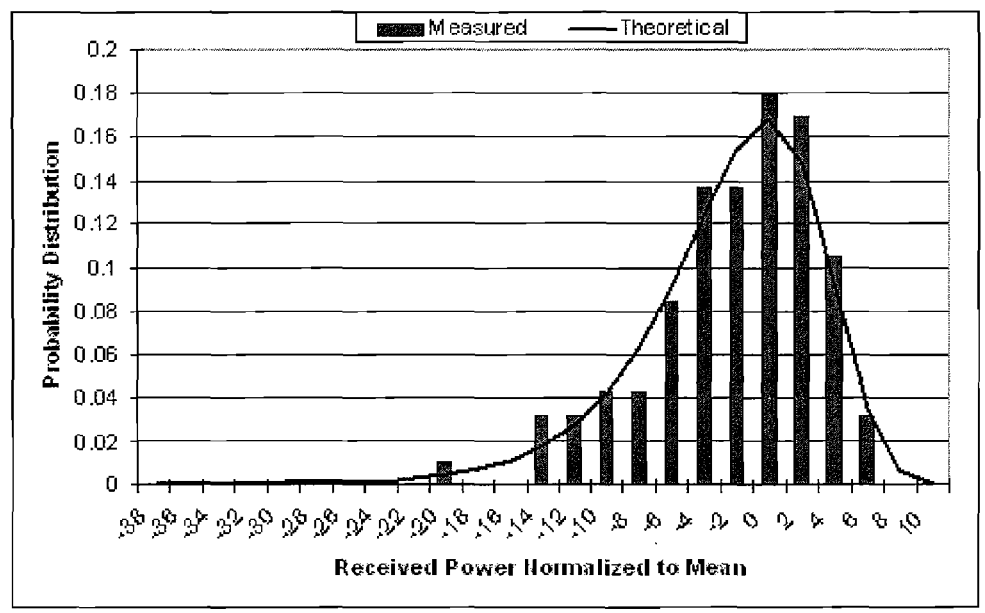
Figure 11. Chi-square distribution of DFS data for 1 GHz at position 1.
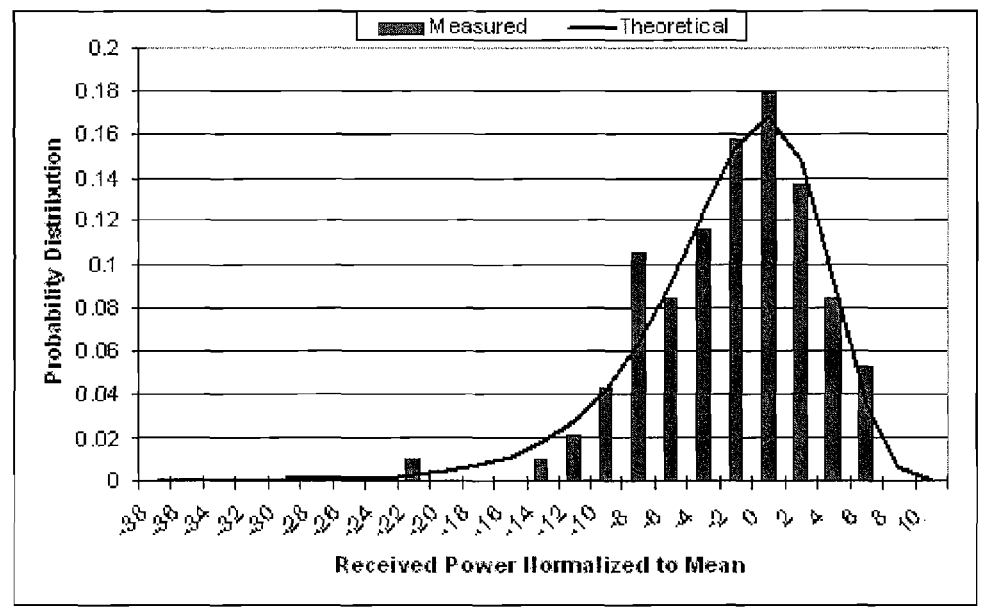
Figure 12. Chi-square distribution of DFS data for 10 GHz at position 1.

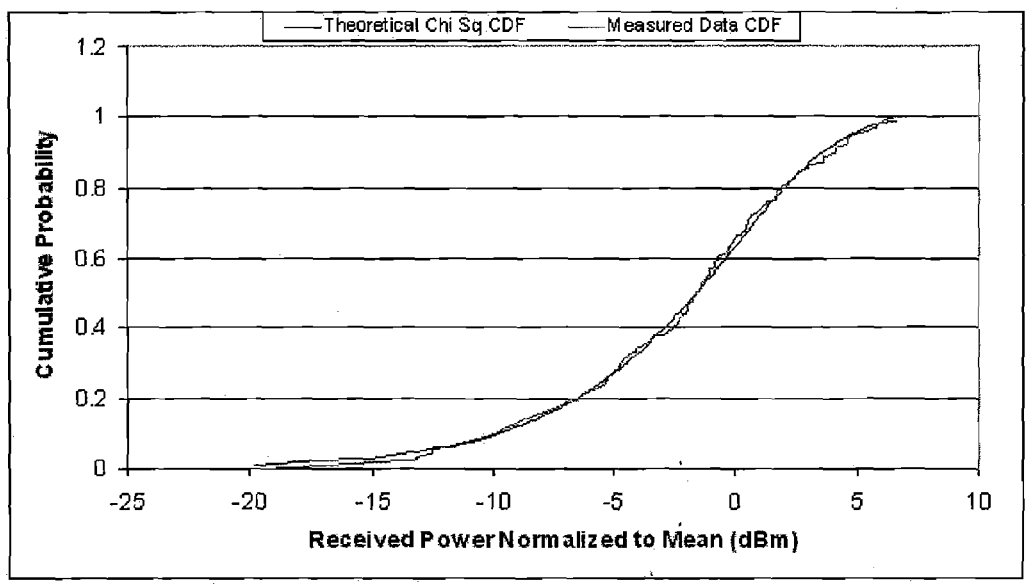
Figure 13. Cumulative distribution of MS data for 1 GHz at position 1.
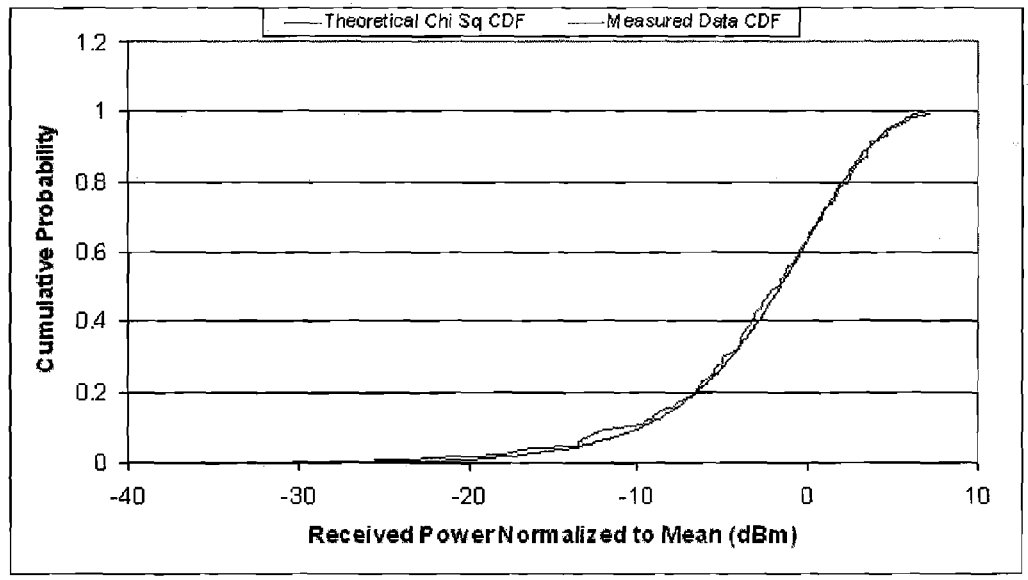
Figure 14. Cumulative distribution of MS data for 10 GHz at position 1.

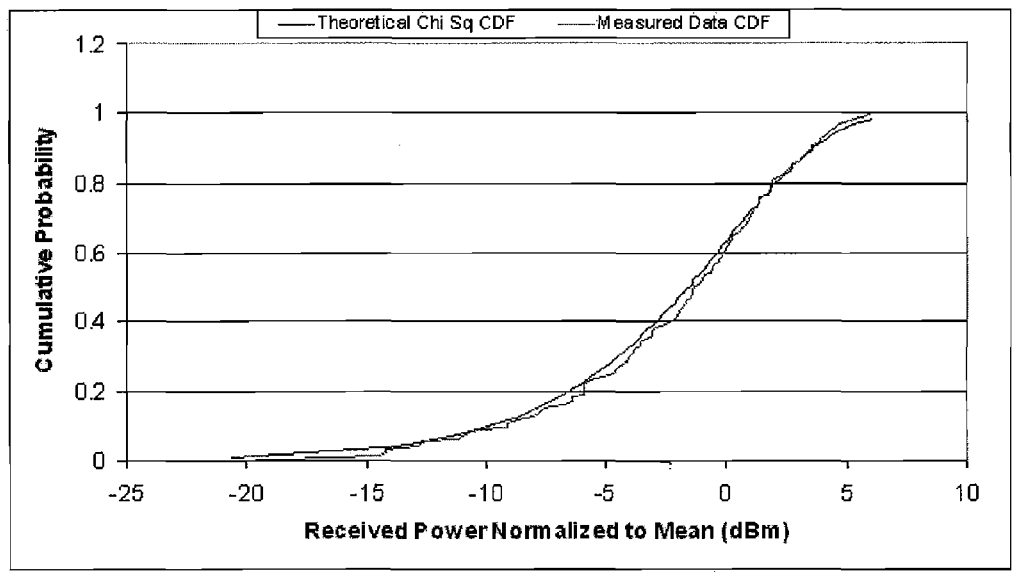
Figure 15. Cumulative distribution of DFS data for 1 GHz at position 1.
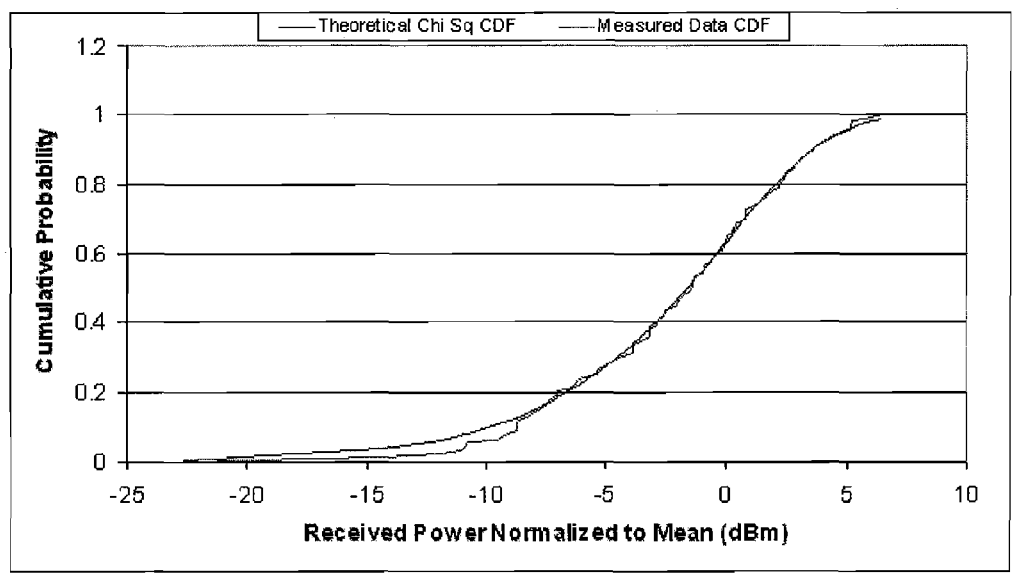
Figure 16. Cumulative distribution of DFS data for 10 GHz at position 1.

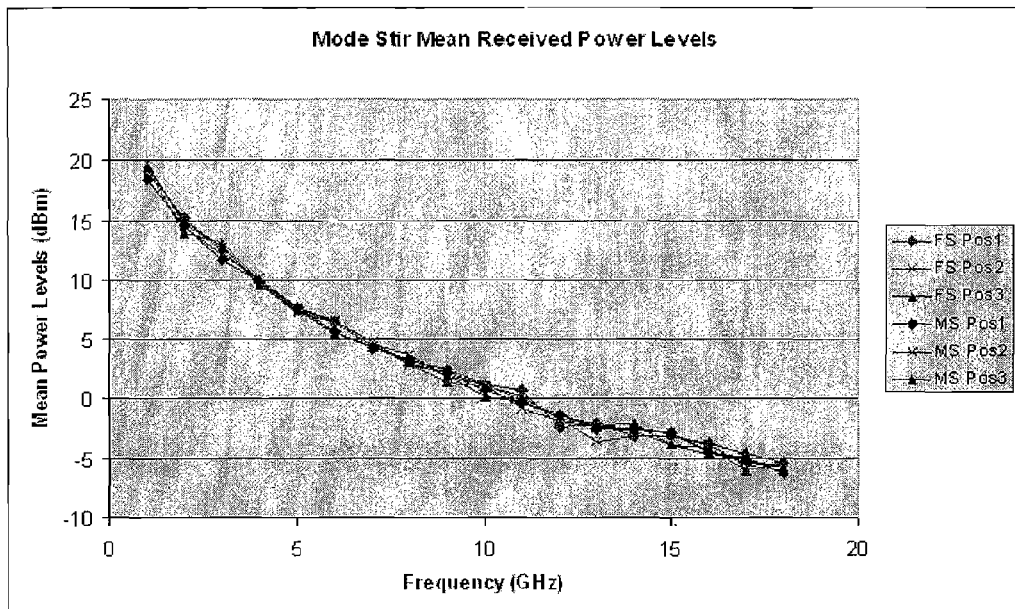
Figure 17. Measured field uniformity.
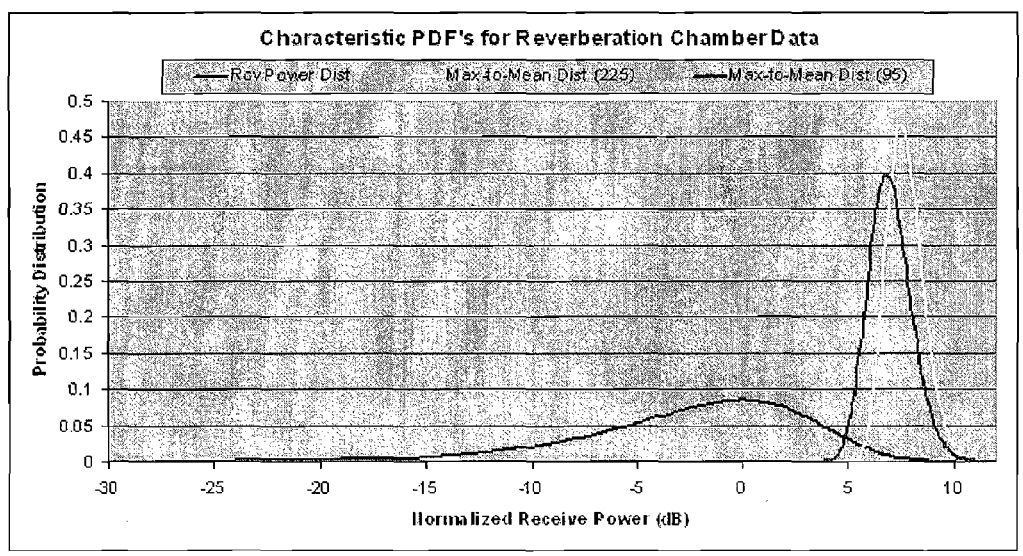
Figure 18. Max-to-mean probability distribution functions.

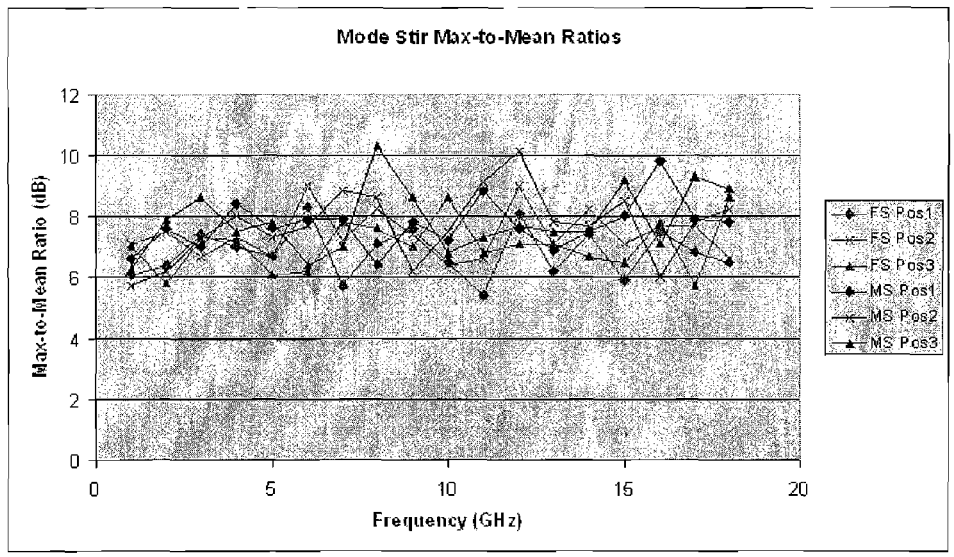
Figure 19. Max-to-mean ratios for all data sets.
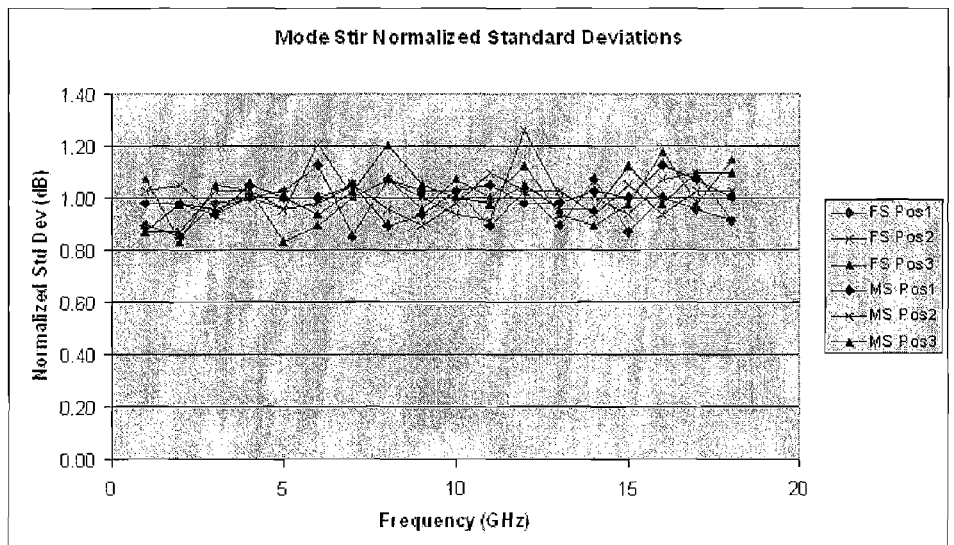
Figure 20. Normalized standard deviations for all data sets.

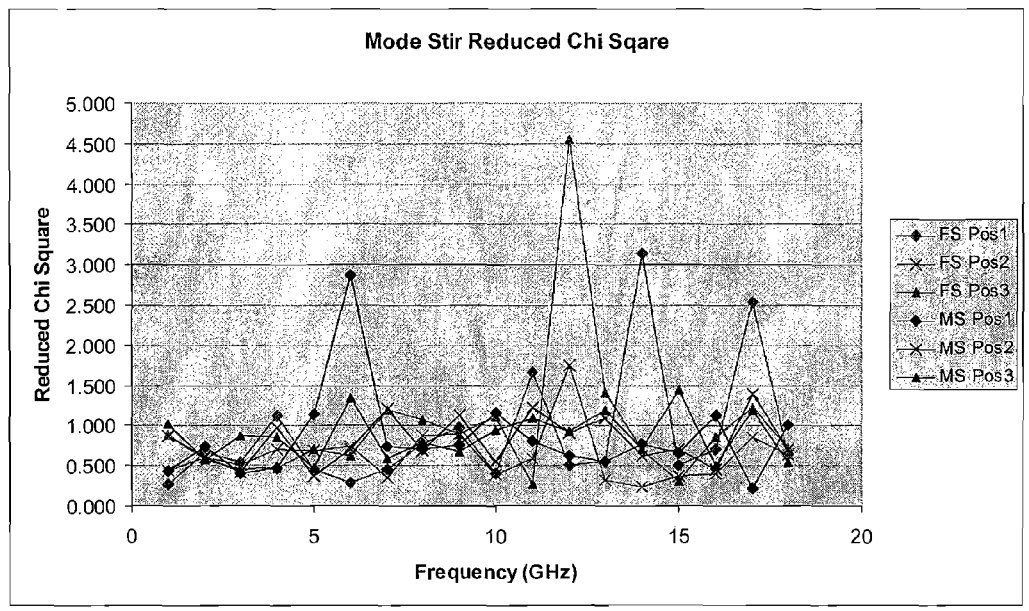
Figure 21. Reduced chi-square statistics for all data sets.
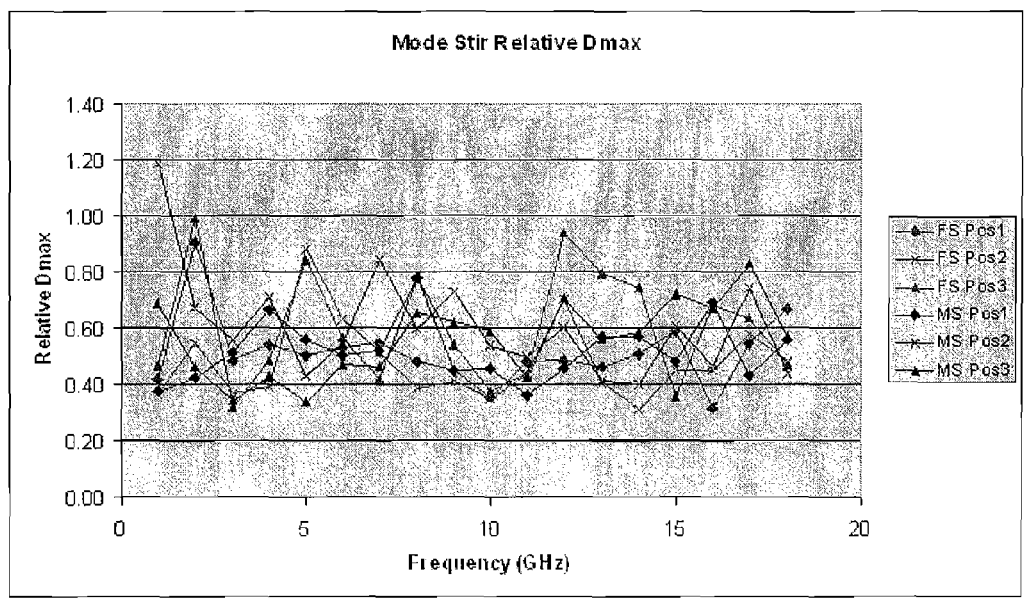
Figure 22. Relative $D_{MAX}$ for all data sets.

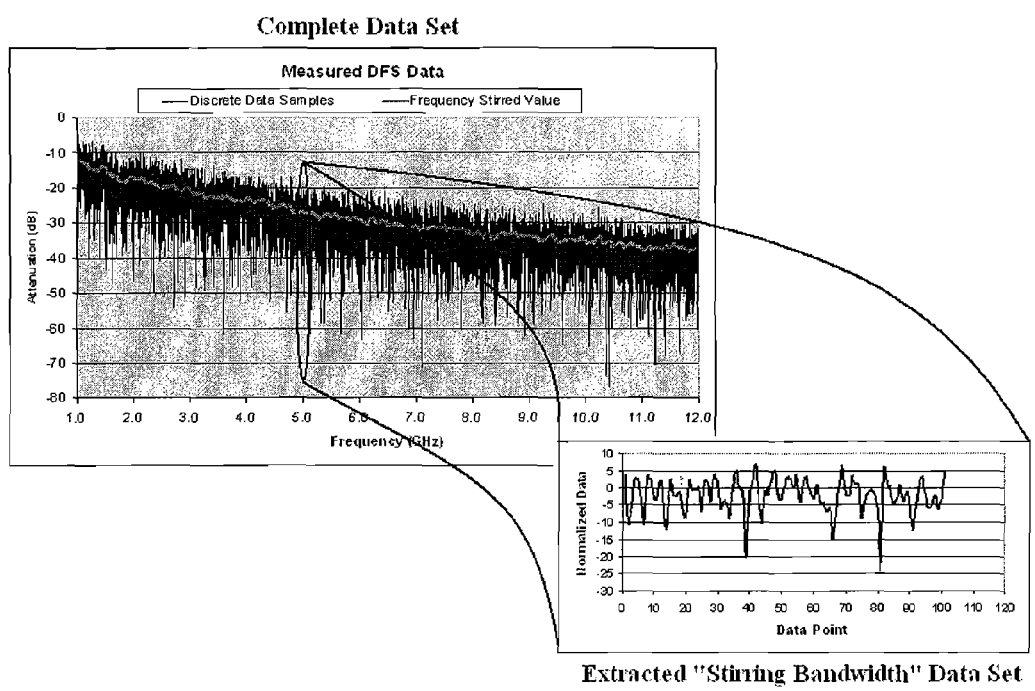
Figure 23. DFS measured data: complete data set and stirring bandwidth data set.

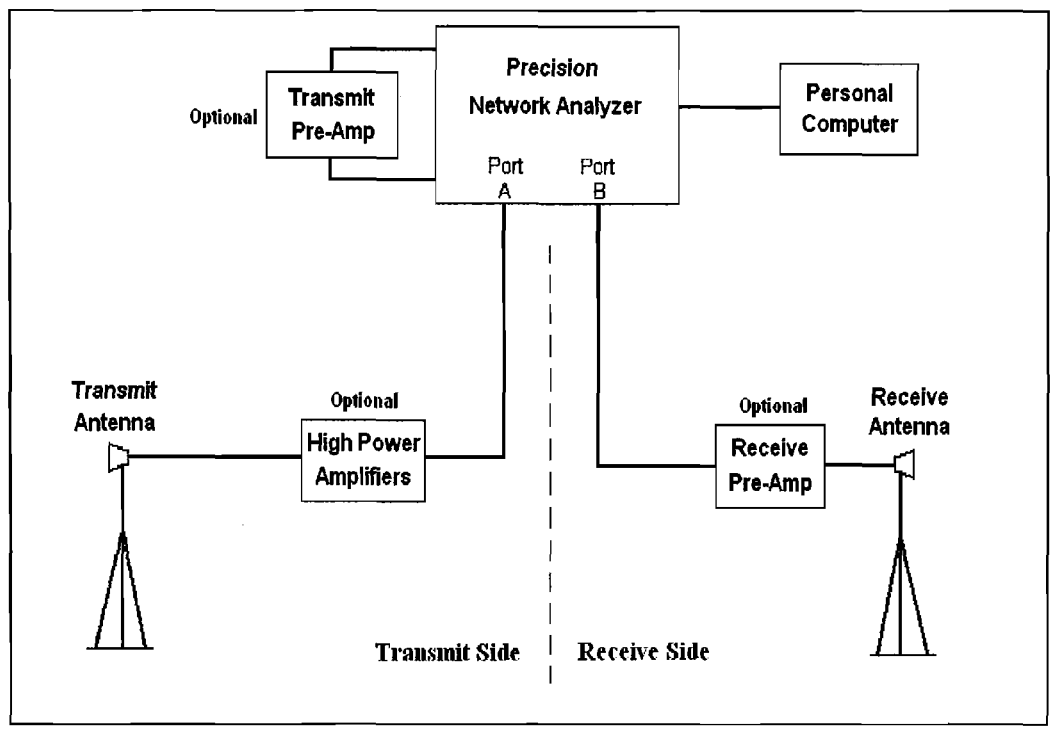
Figure 24. DFS equipment setup.

ELECTROMAGNETIC TESTING OF AN ENCLOSURE OR CAVITY USING A DISCRETE FREQUENCY STIR METHOD

TECHNICAL FIELD

The present invention relates generally to electromagnetic testing of an enclosure or cavity for the determination of select electrical characteristics (e.g. RF shielding characteristics or RF propagation characteristics). More particularly, the present invention is related to an alternative and, in some respects, improved mode stir measurement technique for the performance of such tests.

BACKGROUND OF THE INVENTION

A key problem associated with the measurement of the electromagnetic field inside an electrically large and relatively lossless enclosure is that the field is random and highly variable (with field variations from point to point inside the enclosure). However, the field is also considered to be statistically uniform, for example, the average measured in one general location of the enclosure will be approximately the same as the average measured in another general location within the same enclosure. Because the field is random and highly variable, it is preferable to use a statistical measurement approach to measuring electromagnetic characteristics of an enclosure (e.g., average field level, peak field level, statistical distribution of field levels).

As field mapping locations inside the enclosure would be too time consuming or too equipment intensive, mode stir methods have been widely used for statistical measurement of electromagnetic characteristics of an enclosure. Mechanical mode stirring is the most widely accepted and commonly practiced method of exciting or randomizing the modes in a reverberation chamber to generate a statistically uniform field. Mechanical stir (MS) methods physically alter the boundary conditions within the enclosure to change the distribution of field strengths. This is typically done by the use of an electrically conductive paddle wheel that is rotated at small angular increments. The field is measured at each angular position of the paddle wheel and then the average field strength is determined by averaging over all the measured values obtained through one complete revolution of the paddle wheel.

Mechanical stirring suffers from being time intensive and limited by how well the paddle wheel is designed and used to stir the field. The paddle wheel also adds a level of complexity to the test setup, since its rotation must be synchronized with the measurement equipment and any other paddle wheels used in the test setup.

As an alternative to mechanical mode stirring, frequency stir methods simulate boundary condition variations by changing the wavelength of the excitation source through small increments in excitation frequency. Frequency stirring has traditionally been done by superimposing a band-limited noise signal onto the excitation source which is a single frequency, continuous wave (CW) signal, and then measuring the total power within the bandwidth of the noise signal. By this method, the average field level obtained is taken as the average over all enclosure eigenmodes contained within the measurement bandwidth.

The traditional frequency stir method has limitations associated with the loss of statistical data components and the complexity and performance of the measurement equipment. Because the measurement being made for this method is total power within the noise bandwidth, only the average field level across the noise bandwidth can be determined and the individual field levels that contribute to the total power are not measured. As a result, a statistical analysis of the contributing field levels cannot be made to check the measurement against prevailing mode stir theory. Also, since the excitation source for the traditional frequency stir method is a band-limited noise signal superimposed on a single frequency sine wave, the test equipment setup is more complex, requiring more pieces of equipment including a separate signal generator and receiver. This makes it more difficult to move the measurement equipment for remote area tests. Further, the actual generation of a well defined band-limited noise signal can be problematic (especially at higher frequencies, i.e., above 10 GHz). Since the measurement is a broadband measurement, this technique suffers more than the others from dynamic range limitations and possible noise interference (when used at open area test sites).

SUMMARY OF THE INVENTION

The present invention provides the "discrete frequency stir" (DFS) method for improved mode stir testing of an enclosure or cavity. Adequate sampling of the electric field inside the enclosure or cavity is provided for by electronic perturbation or "stirring" of the field. This stirring is accomplished by exciting the enclosure or cavity with a short duration, continuous wave, radiated source where the continuous wave frequency is stepped in small frequency steps across a frequency range of interest. The frequency steps are selected to be at least slightly larger than the resonant mode bandwidth associated with the given enclosure or cavity in order to provide statistically independent measurements. A stirring bandwidth is selected to encompass a statistically significant number of these measurement samples while maintaining adequate frequency resolution. A statistical evaluation of the measured field is then performed over this stirring bandwidth. For example, the average field level at a given frequency is determined by averaging over the samples contained within the stirring bandwidth when centered on that frequency.

The DFS method is particularly suited to accurately measure the average field level within an electrically large, "lossless" enclosure and determine the peak field level statistically from the measured data. Relatively lossless enclosures can include reverberation chambers, aircraft cavities (such as the avionics bay or passenger cabin), and launch vehicle payload areas. As such, the DFS measurement method is applicable to aircraft shielding measurements, RF propagation measurements, component level shielding measurements (e.g., window treatments, EMI gaskets, etc.), electrical properties extraction for electrically large and complex structures, and radiated immunity testing.

Since only a stepped frequency excitation source is required to make the DFS measurement, a network analyzer can be used for both source signal generation and field measurement, resulting in a highly simplified test setup. However, since a small frequency step size is required and a large frequency range is typically required for the applications considered, the more recent generation of precision network analyzer is preferred for performing this measurement since it can store a large number of data points.

The DFS method provides significant advantages over other mode stir methods in terms of its simplified test setup and reduced test time, and in some cases performance advantages are realized as well. Compared to mechanical stirring, the DFS method does not require time-intensive and complex, synchronized control of a paddle wheel. Compared to traditional frequency stirring, the DFS method offers a simplified equipment setup since only a single frequency, continuous wave source is used rather than a band-limited noise source. With the DFS method, both excitation signal generation and field measurement can be done easily with a network analyzer, whereas with traditional frequency stir, signal generation requires both a noise source and continuous wave signal source and then a separate measurement device. In addition, the DFS method typically offers improved dynamic range since measurements are done with a narrower bandwidth limiting the environmental or equipment noise that is added to the measurement. Another technical benefit is that the DFS method allows for statistical analysis of the measured field whereas traditional frequency stir does not. The DFS method is also faster than the traditional frequency mode stir method.

The present invention as a whole, together with its further objects and attendant advantages, will be best understood by reference to the following detailed description taken in conjunction with the accompanying drawing Figures, in which the same reference numerals are used to refer to the same components.

BRIEF DESCRIPTION OF THE DRAWINGS

FIG. 1 shows the frequency, and therefore the mode density, for the first 150 resonant modes of a small sample chamber where the resonant mode frequency is calculated according to equation (3).

FIG. 2 shows the calculated mode density, reduced number of effective modes, and resonant mode bandwidth for the small sample chamber according to equations (5), (7), and (6), respectively.

FIG. 3 shows actual resonant cavity modes existing within a 100 MHz bandwidth centered at 1 GHz.

FIG. 4 shows a 2D cross-sectional visualization for the mode TM11,2,0 at 0.954 GHz.

FIG. 5 shows a 2D cross-sectional visualization for the mode TM6,9,0 at 1.022 GHz.

FIG. 6 shows a test setup for Mechanical Stir (MS) measurements of the small sample chamber for comparison to DFS measurements.

FIG. 7 shows an example of the MS received power over one complete paddle revolution at one frequency.

FIG. 8 shows an example of the DFS received power for 1 to 4.5 GHz at one position.

FIGS. 9 and 10 show graphs of the $\chi^2$ distributions for MS data sets for 1 GHz and 10 GHz, respectively.

FIGS. 11 and 12 show graphs of the $\chi^2$ distributions for DFS data sets for 1 GHz and 10 GHz, respectively.

FIGS. 13 and 14 show cumulative distribution graphs for MS data sets for 1 GHz and 10 GHz, respectively.

FIGS. 15 and 16 show cumulative distribution graphs for the corresponding DFS data sets for 1 GHz and 10 GHz, respectively.

FIG. 17 shows mean received power levels across the 1-18 GHz range for both MS and DFS measurements at the three test measurement locations.

FIG. 18 shows the $\chi^2$ probability distribution function for the received power along with the probability distribution for the max-to-mean ratio for both MS and DFS data sets.

FIG. 19 shows the max-to-mean ratios for all data sets.

FIG. 20 shows the mean normalized standard deviation for all measured data sets.

FIG. 21 shows the reduced chi-square statistic for all data sets.

FIG. 22 shows the relative $D_{MAX}$ statistic for all data sets.

FIG. 23 illustrates a complete set of measured data for a given DFS test covering 1 to 12 GHz using a frequency step size of 1 MHz, and also shows a "zoomed-in" view of the data associated with the stirring bandwidth at 5 GHz where the measured values have been normalized to the average value for that stirring bandwidth.

FIG. 24 illustrates schematically an equipment setup for conducting tests using the discrete frequency stirring method.

DETAILED DESCRIPTION OF THE INVENTION

Background: Mode Stir Introduction

Mode stir methods are used to generate statistically uniform fields within electrically large, relatively lossless enclosures or cavities for conducting electromagnetic testing. Mode stir techniques have been used extensively within the reverberation chamber environment for radiated immunity and emissions testing of electrical equipment, as well as shielding effectiveness measurements of screens, windows, cable shields, etc. Reverberation chambers are specific instances of an electrically large, high Q cavity that support a large number of normally distributed eigenmodes (TE and TM modes) with zero mean and equal variances. The large number of modes combine (in a vector summation sense) to generate a randomized electromagnetic environment within the cavity. Perturbation of this modal structure, commonly called mode-stirring, by changing either the geometry of the cavity (mechanical mode stir) or the frequency of the excitation source (electrical or frequency mode stir) will cause the field level or measured power at a given location within the cavity to vary statistically, equivalent to spatial mapping of the cavity. By adequately stirring the modes, the complete range of field levels that exist within the cavity based on the excitation source and the cavity geometry can be observed at a given location. This distribution of field levels can then be expected at any location within the cavity (that is adequately removed from the conducting walls), providing the statistically uniform field.

Background: Theoretical Cavity Field Distributions

Theory predicts that the magnitude of any of the electric field components (x, y, or z) is $\chi$ distributed indicating the received power to be $\chi^2$ distributed, both with two degrees of freedom. The $\chi^2$ probability density function (PDF) is as follows:

$$f(p) = \frac{1}{2\sigma^2} e^{-p/2\sigma^2} \quad (1)$$

where p is the received power and $\sigma$ is the standard deviation of the underlying normal distributions. Measurements of the received power are commonly viewed in log magnitude format so the variable substitution P=10 log (p) is appropriate. The corresponding modification of equation (1) is:

$$f(P) = \frac{1}{\beta} e^{(P-\bar{P})/\beta} \cdot e^{-e^{(P-\bar{P})/\beta}} \quad (2)$$

where P bar is the mean received power and $\beta=10/\ln 10=4.34$. As can be seen from equation (2), the $\chi^2$ distribution has the amiable characteristic of being completely described by its mean. Therefore, with accurate determination of the mean field within the cavity, by some statistically significant sampling of the field, then the spread of the data, including its maximum value, can be known to a specified confidence level.

Background: Cavity Resonant Mode Theory

Mode stir methods rely on the mode structure within the cavity being measured. For rectangular cavities, the frequencies of the resonant cavity modes can be calculated by:

$$f_{lmn} = \frac{1}{2\sqrt{\varepsilon\mu}} \sqrt{\left(\frac{l}{a}\right)^2 + \left(\frac{m}{b}\right)^2 + \left(\frac{n}{c}\right)^2} \quad (3)$$

where l, m, and n are integers and a, b, and c correspond to the cavity dimensions, specifically the length, width, and height, respectively, for the chamber considered here. For a small sample chamber with rectangular dimensions (length×width×height) of 1.8×1.5×2.3 meters, the frequency of the lowest resonant mode is 107.3 MHz which corresponds to the TE101 mode. The first 150 modes for the small sample chamber are shown in FIG. 1.

An estimation of the field uniformity based on the number of independently excited modes within the cavity has been developed with prior mode stir tests. Essentially, the more propagating modes that are available for excitation, the higher the potential for good field uniformity will be. The number (N) of available modes in a cavity can be estimated by the classical Weyl approximation given as follows:

$$N = \frac{8\pi V}{c^3} f^3 \quad (4)$$

where V is the volume of the cavity, c is the speed of light, and f is the excitation frequency. However, the derivative of the number of available modes, the mode density (dN) is more useful in determining the field uniformity. The mode density describes the number of available modes within a small bandwidth of frequency centered around the excitation frequency of the cavity and is determined by:

$$dN = \frac{8\pi V}{c^3} f^2 df \quad (5)$$

where df is the bandwidth over which the modes are stirred, the excitation source bandwidth. In the ideal lossless cavity case, a discrete frequency CW source, as is used for mechanical stir measurements, would have zero bandwidth. However, for real cavities with loss, the CW signal bandwidth will be the cavity resonant mode bandwidth ($BW_Q$) which can be approximated as follows:

$$BW_Q = \frac{f}{Q} \quad (6)$$

where f is the excitation frequency (in Hz) and Q is the quality factor of the cavity. When the resonant mode bandwidth is used for df in equation (5), the number of excited modes is referred to as the specific mode density. The specific mode density does not typically excite a large enough number of modes to generate good field uniformity, but MS techniques rely on physically changing the boundary conditions of the cavity to effectively excite a sufficient number of resonant modes.

Traditional frequency stir measurements utilize a frequency (noise) modulated source with bandwidths usually in the 10 MHz to 100 MHz range to excite a large number of resonant modes in accordance with equation (5). However, using these noise source bandwidths for df in equation (5) can over-predict the number of independently excited modes due to the non-zero bandwidth of the resonant modes. This has been accounted for by taking the ratio of the excitation source bandwidth to the bandwidth of the resonant modes resulting in a reduced number (NQ) of effective modes according to:

$$N_Q = \frac{BW_{svc}}{BW_Q} \quad (7)$$

where $BW_{src}$ is the bandwidth of the excitation source. The lesser of dN and NQ should be used to determine the number of independently excited modes in the cavity.

The excitation source bandwidth of the traditional frequency stir method is equivalent to the stirring bandwidth of the DFS method. For a 100 MHz stirring bandwidth, the mode density, reduced number of effective modes, and resonant mode bandwidth pertinent to the small sample chamber were calculated and are shown in FIG. 2. The actual resonant cavity modes that exist within a 100 MHz bandwidth centered at 1 GHz were calculated in accordance with equation (3) and are shown in FIG. 3.

The ordering of the modes is referenced along the 3 spatial directions (x, y, z). A zero order mode has no variation, a 1st order mode has one complete field variation (from null to peak and back to null) or two nodes, a 2nd order mode has 2 complete field variations or 3 nodes, etc. 2D cross-sectional visualizations for two of these modes, TM11,2,0 at 0.954 GHz and TM6,9,0 at 1.022 GHz, are shown in FIGS. 4 and 5 respectively. For example, in FIG. 4, the TM11,2,0 mode has 12 nodes along the x-axis, 3 nodes along the y-axis, and no field variation along the z-axis (oriented with positive z pointing into the plane of the figure). These figures clearly show the variation in field levels that can be experienced at a given location within the chamber as the frequency of the excitation source is changed.

Discrete Frequency Stirring Method

Mode stir test methods rely on the theoretical field distributions and mode structure of electrically large, lossless enclosures or cavities to make a statistical assessment of the electromagnetic fields within those enclosures or cavities. In the present invention, the method of discrete frequency stirring (designated as "DFS") provides improved mode stir testing. With the DFS method, the enclosure or cavity is excited with a short duration, continuous wave, radiated source. The frequency of this excitation source is stepped at small frequency steps across a frequency range of interest. The frequency steps are selected to be at least slightly larger than a resonant mode bandwidth associated with the given enclosure or cavity in order to provide statistically independent measurements. A stirring bandwidth is selected to encompass a statistically significant number of these measurement samples while maintaining adequate frequency resolution in the subsequent analysis data. Statistical evaluations of the measured field are performed over the stirring bandwidth. For example, the average field level at a given frequency is determined by averaging over the samples contained within the stirring bandwidth when centered on that frequency.

The frequency range for any given DFS test is constituted by the complete range of frequencies over which measurements are desired to be made for a particular enclosure or cavity in an application or environment of interest for electromagnetic testing. This range of frequencies is often based on some desired frequency response of the enclosure under testing. For example, when testing an aircraft for shielding against radio frequency threats found near an airport, the frequency range may cover 100 MHz to 10 GHz which spans airport related communication, navigation, and surveillance radar frequencies. The range of frequencies may also be governed by a specific certification or qualification requirement. For example, when testing electrical equipment for radiated immunity based on governmental standards for RTCA DO-160 or MIL-STD-461 requirements, the frequency range would be as described in those standards.

The resonant mode bandwidth is the bandwidth of the individual resonant modes associated with the cavity/enclosure of concern in the DFS test. The resonant mode bandwidth is based on the quality factor (Q) of the cavity and is used to determine the frequency step size of the excitation source. The Q of the cavity is know from previous measurement or can be analytically estimated according to standard formulations based on physical size and electrical properties. The resonant mode bandwidth ($BW_Q$) is analytically estimated according to theory as in equation (6). For example, high Q cavities such as reverberation chambers can have resonant mode bandwidths in the range of 10 KHz to 1 MHz across the frequency range of 100 MHz to 18 GHz, and moderate Q cavities such as commercial aircraft interiors can have resonant mode bandwidths in the range of 200 KHz to 10 MHz for the same frequency range.

In the performance of a DFS test, stepping the frequency of the excitation source at intervals at least slightly larger than the resonant mode bandwidth will result in sample independence. Sample independence is necessary to perform statistical analysis on the measured data. Verification of sample independence is accomplished by an autocorrelation check of the measured data, such as the Pearson's r autocorrelation check:

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad (8)$$

where the x's represent a measured data set within a given stirring bandwidth and the y's represent the same data set except shifted up one so that $x_2$ has become $y_1$, $x_3$ has become $y_2$, etc. For the Pearson's r check, the data is typically taken to be uncorrelated when r is less than 1/e=0.367. An r equal to zero indicates that the data is totally uncorrelated. Correlated data would suggest that the resonant mode bandwidth was not correctly estimated and the subsequent frequency step size that was chosen was too small. If that is the case, measurements can be made again at a larger frequency step size (based on an improved estimate of the resonant mode bandwidth) or the correlated data set can be sifted (at every other data point, or every 3rd data point, etc.) to obtain an uncorrelated data set.

The stirring bandwidth is that frequency band over which the frequency stirred, or average, field value is determined. The stirring bandwidth is typically a small sub-band of the entire frequency range of a DFS test. Ideally, the stirring bandwidth is chosen to be small enough so that the average field value within the cavity of concern is considered to be constant across the stirring bandwidth. In practice, the stirring bandwidth is chosen to be large enough to contain a statistically significant number of samples (i.e. for the performance of statistical analysis, such as the autocorrelation check discussed above, which are calculated with only the measured data samples that fall within the stirring bandwidth, not the complete data set covering the entire frequency range) considering the frequency step size required for sample independence, but must also be small enough to maintain the desired frequency resolution in the averaged field values (i.e. small enough so as not to "average out" the resonant effects of apertures of concern, etc.). A stirring bandwidth containing at least 100 measurements is typically desired and has been found to be adequate for statistical analysis purposes.

FIG. 23 shows an extracted plot of the measured DFS data that falls within a 100 MHz stirring bandwidth centered at 5 GHz (note the "extracted" plot shows data that has been normalized to the average value at 5 GHz). The frequency step size used to collect the data in FIG. 23 was 1 MHz, providing 101 measurement samples within the stirring bandwidth which was set to 100 MHz (for DFS measurements made to date in reverberation chambers and aerospace cavities, a stirring bandwidth of 20-50 MHz has typically been used below 1 GHz and a stirring bandwidth of 100-200 MHz has typically been used above 1 GHz). It should be noted here that the average, or frequency stirred, value for a given stirring bandwidth is assigned to the center frequency of that bandwidth. In this manner, the frequency range beginning and end points, to ± half the stirring bandwidth, respectively, will not have associated average values since these points do not have complete stirring bandwidth data sets.

Implementation of the DFS Method

Implementation of the DFS method preferably employs a precision network analyzer, which is used for both generation of the excitation signal and measurement of the field inside the enclosure of interest. FIG. 24 shows a typical test equipment setup for a DFS test. The DFS method requires that the network analyzer be able to measure and store a large number of data points for a given frequency sweep, on the order of 10,000 points. This has only recently been made possible with the newer network analyzer models (older network analyzers can store on the order of 1000 data points). The Agilent Precision Network Analyzer (PNA), model E8362B with Option 14, was used during development of the DFS method and is recommended for continued DFS method implementation. This PNA can measure up to 16,001 data points per measurement channel and will cover the frequency range of 10 MHz to 20 GHz, which is sufficient for most current aerospace applications. Option 14 provides front panel access which allows for the inclusion of a transmit path pre-amp prior to measurement of the transmit port (Port A) signal level. This option is recommended to provide increased dynamic range while negating any measurement variation due to transmit pre-amp fluctuations.

The excitation signal is transmitted from Port A to the transmit antenna (via high power amplifiers if desired for increased dynamic range). The excitation signal is a short duration, continuous wave signal, stepped in frequency to cover the frequency range of interest. The stepped frequency excitation source is the mechanism for field perturbation with the DFS method. The frequency step size is critical to statistical analysis of the measured data and is determined as noted previously. The transmit antenna is used to introduce the excitation signal into the test environment and care should be taken to eliminate, as much as is practical, direct path coupling between the transmit and receive antennas.

The receive antenna is used to sample the field inside the enclosure of interest for each frequency step. A receive pre-amp may be used to amplify the received signal if increased dynamic range is desired. The actual measurement that is made is the network analyzer S21 measurement which is a ratio of the signal level at Port B to the signal level at Port A. This measurement is commonly referred to as the attenuation (or gain) of the RF signal between the two ports. If there is significant impedance mismatch between the transmit antenna and the rest of the measurement system then the attenuation (S21) measurement should be corrected to account for the reflected signal at the transmit antenna. To do this the network analyzer reflection measurement, the S11 measurement, must also be made. The corrected received power can then be determined as:

$$P_{r,corr} = \frac{|S_{21}|^2}{1-|S_{11}|^2} \quad (9)$$

where $P_{r,corr}$ is the corrected received power that will be used for further analysis and S21 and S11 are the raw measurements. Finally, with regard to FIG. 24, the personal computer that is shown is used to download the measured data (S21 and S11 measurements) for storage and data processing.

To expand on a point made previously, field perturbation or "stirring" via the DFS method is accomplished through small changes in excitation source frequency. Measurement of the field is made at a given location for each discrete frequency that is generated. For measurements within a small range of frequencies, this is equivalent to moving the receive antenna around to multiple locations within the enclosure and measuring the field level for just one frequency (i.e. the same range of field amplitudes and distribution of those amplitudes will be measured). So for the DFS method, the average field level is determined by averaging over the discrete frequency measurements that fall within a small portion of the entire frequency range being measured. This small band of frequencies used to determine the average field level at any given (center) frequency is designated as the stirring bandwidth. The stirring bandwidth can be changed across the frequency range being measured as is deemed appropriate to accommodate frequency dependant effects of the enclosure or cavity (for example, the resonant mode bandwidth of the enclosure of cavity under test may change with frequency requiring an adjustment of the stirring bandwidth to maintain an adequate number of samples within the stirring bandwidth). Factors to consider in setting the stirring bandwidth have been discussed above. Note that all statistical analyses (i.e. determination of average field level, field distribution assessment, data correlation assessment, etc.) of the field inside the enclosure at a given frequency is also performed with the discrete frequency measurements that fall within the stirring bandwidth.

Since it is the discrete frequency measurements within the stirring bandwidth that are used to determine the average field level and other field statistics, it is important that the frequency step size between subsequent measurements be large enough to account for the resonant mode bandwidth and produce independent measurements, as noted previously. The frequency step size of the excitation signal can be controlled by network analyzer settings (frequency range and number of data points) to produce independent measurements. By stepping the excitation source frequency at slightly greater than the resonant mode bandwidth of the enclosure being investigated, the maximum number of independent measurements of the field inside the enclosure for a given stirring bandwidth can be made.

Validation of DFS against MS Measurements

Mechanical stirring (MS) is a widely accepted and commonly practiced method of performing a mode stir test in a reverberation chamber. With mechanical stir, field perturbation or "stirring" is effected by physically changing the boundary conditions of the enclosure/cavity under test, typically by the rotation of an electrically large paddle wheel. A comparison of mechanical stir data and DFS data was made to validate the DFS method against current "best practices" and prevailing theory. This comparison was facilitated by making both mechanical stir and DFS measurements inside a small reverberation chamber with dimensions (l×w×h) of 1.77× 1.52×2.29 meters. This chamber is owned and operated by the Boeing Metrology Lab in Seattle, Wash., and is referred to herein as the "small sample chamber". The small sample chamber is shown in FIG. 6. Comparisons to theory were made for both methods by performing chi-square and Kolmogorov-Smirnov goodness-of-fit tests to the expected distribution, and by examining other mode stir characteristics such as field uniformity, max-to-mean ratios, and the standard deviation of the measurements. Measurements for the comparison were made across the 1-18 GHz frequency range.

For the MS measurements, a moderately sized paddle wheel consisting of four paddles with a total surface area of 2.85 m² was located at the top of the chamber and attached to the top surface. Two EMCO 3115 horn antennas were used as the transmit and receive antennas, and were placed inside the cavity in an orientation that prevented direct path coupling. An HP8510 network analyzer was used to step a CW signal from 1 to 18 GHz (where the chamber volume could support a large number of modes) in 1 GHz steps. The paddle and network analyzer were controlled from a PC. A total of 225 paddle positions were used to make one complete revolution of the paddle wheel. At each paddle position, the network analyzer stepped though all measurement frequencies before the paddle was moved to the next position (each measurement was made at a slightly different paddle rotation angle to provide the variable geometry needed to stir the modes). Once measurements had been made for a complete paddle rotation at each frequency step, the receive antenna was moved to a different location and the measurements were repeated. A total of three receive antenna locations (designated Positions 1, 2, 3) were measured. In this manner, the raw measurement data consisted of real and imaginary S21 and S11 (complex voltage) measurements made with the network analyzer for each paddle position at each frequency at the three receive locations.

The DFS data acquisition was performed in a very similar manner to the MS measurements except that the MS paddle was not moved during the DFS measurements, and the Agilent PNA (model E8362B with Option 14) was used instead of the HP 8510. From FIG. 2, it can be seen that the resonant mode bandwidth for the small sample chamber was below 1 MHz across the 1-18 GHz frequency band so the frequency step was required to be at least 1 MHz. With this requirement and the PNA measurement capabilities, the 1-18 GHz frequency range was measured with one sweep, using 16001 measurement points, which resulted in a frequency step size of about 1.1 MHz. With this setup, 95 independent frequency measurements were made within the 100 MHz stirring bandwidth that was used for the statistical analysis of the DFS data. Again, the raw measurement data consisted of real and imaginary S21 and S11 measurements. As with the MS measurements, three different receive locations were measured, being approximately the same locations used during the MS measurements.

Validation of DFS against MS Measurements: Measured Data

For both MS and DFS measurements, since a strict measure of the attenuation experienced by the field in the chamber was desired, the network analyzer data were corrected for reflection from the transmit port according to equation (9), so that the corrected received power was actually used in the statistical analysis. FIG. 7 shows an example of the MS received power over one complete paddle revolution at one frequency. FIG. 8 shows an example of the DFS receive power for 1 to 4.5 GHz at one position. The data sets for the MS measurements consisted of 225 measured received power levels corresponding to the 225 paddle positions, and the data sets for the DFS measurements consisted of 95 received power levels corresponding to the number of individual frequency measurements that fell within the 100 MHz stirring bandwidth. For all data sets, the mean, variance, and standard deviation were calculated according to standard numerical formulas. The received power data was then normalized to the mean and sorted (using Excel's sorting function) from smallest to largest to be used in the goodness of fit tests.

Auto-correlation checks of the unsorted received power data were performed since the theoretical $\chi^2$ distribution of the data depends on the evaluation of an adequate number of independent samples. To accomplish this, the Pearson's r correlation coefficient was calculated according to equation (8). This was done for 25 consecutive shifts; each shifted data set was compared with the unshifted data (i.e. data set shifted by 5 from the original was not compared with the data set shifted by 4, but with the original data set). The measured data was found to be uncorrelated based on the 1/e criteria for all (both MS and DFS) data sets used for the comparison.

Validation of DFS against MS Measurements: Goodness-of-Fit Tests

Two goodness-of-fit tests were used to compare the MS and DFS measured data to the theoretical field distributions. The chi-square goodness-of-fit test between data and a distribution function is performed by calculating the $\chi^2$ statistic as follows:

$$\chi^2 = \sum_{i=1}^{m} \frac{(k_i - n_i)^2}{n_i} \tag{10}$$

where m is the number of data bins, $k_i$ is the number of measured samples in the ith bin (always an integer), and $n_i$ is the expected number of samples in the ith bin based on the suspected distribution function; in this case the $\chi^2$ distribution of equation (2). For all MS and DFS data sets, the spread of mean normalized power fell between −38 dBm and 10 dBm, so this range of power levels was divided into bins and used to compute the 2 statistic for each data set. A bin size of 2 dB was chosen to give an adequate number of bins while not depleting the number of samples in each bin too severely, the exception being in the tail regions where some bins contain no measured data samples. Numerical integration using a 3-pt Simpson's rule was used to determine the expected number of samples in each bin as follows:

$$n_i = h\left[\frac{1}{3}f_0(P) + \frac{4}{3}f_1(P) + \frac{1}{3}f_2(P)\right] \tag{11}$$

where $f_1$ represents evaluation of equation (2) at the center of the bin, $f_2$ the equation evaluated at 1 dB above the center of the bin, and $f_0$ the equation evaluated at 1 dB below the center of the bin, and h was the separation between evaluation points (h=1 in this case). The $n_i$'s were then multiplied by the total number of samples to be compared with the number of measured samples in each bin. This caused a reduction in the degrees of freedom (DOF) so that the DOF=m−1 for the determination of the reduced $\chi^2$ used to determine confidence levels (CL's).

Graphs of the $\chi^2$ distributions for two MS data sets are shown in FIGS. 9 and 10, and for the two corresponding DFS data sets in FIGS. 11 and 12. The calculated $\chi^2$ statistics and corresponding confidence level (CL) indicators are provided in appended Tables 1-7 for the various measurement-receive locations for both methods.

The Kolmogorov-Smirnov goodness-of-fit test (commonly referred to as the K-S test) between data and a distribution function is performed by calculating the $D_{MAX}$ statistic. The $D_{MAX}$ statistic is defined at the absolute value of the maximum difference between the theoretical cumulative distribution function and the cumulative distribution function generated from the measured samples. The $\chi^2$ cumulative distribution function (CDF) is given by the standard formulation as:

$$CDF(P) = 1 - e^{-eP/434} \tag{12}$$

The cumulative distribution function of the measured samples is generated by incrementing from zero by 1/N (where N is the total number of samples) at each measurement value. Both functions are plotted against the mean normalized received power. For reverberation chamber data, the commonly accepted criteria for passing the K-S test is:

$$D_{MAX} < \frac{1.22}{\sqrt{N}} \tag{13}$$

These criteria appear to correspond to a CL of 90% statistical agreement with the $\chi^2$ distribution. Cumulative distribution graphs for two MS data sets are shown in FIGS. 13 and 14, and the cumulative distribution graphs for the two corresponding DFS data sets are shown in FIGS. 15 and 16.

Validation of DFS against MS Measurements: Comparison of Results

Tables 1-6 summarize the statistical evaluation of the measured data. The characteristics of the measured field including the maximum, mean, and minimum field levels, the normalized standard deviation, and the max-to-mean ratio, along with goodness of fit evaluations for measured field distributions with respect to the chi-square tests and K-S tests are provided for each MS measurement frequency (i.e. 1, 2, 3, ... 18 GHz) and for all three measurement positions. Tables 1-3 provide the MS data, and Tables 4-6 provide the DFS data.

Mean received power levels across the 1-18 GHz range for both MS and DFS measurements at all three measurement locations are shown in FIG. 17. The data shows that good field uniformity was achieved across the band by the DFS measurement technique comparable to the MS measurement method. The largest variation in the field for the MS technique was 1.1 dB while the largest variation in the field for the DFS technique was 1.6 dB.

As noted previously, correlation between the number of cavity modes excited by the measurement technique and the expected field uniformity has been established. FIG. 2 shows the number of excited modes within the small sample chamber based on a stirring bandwidth of 100 MHz, which was used for the DFS measurements, to vary from about 400 at the low frequency end (1 GHz) to about 100 modes at the high end. This would correlate to an expected field uniformity of about 1.3 dB at the low end to about 2.3 dB at the high end. The measured data

TABLE 1

MS measurement statistics at position 1.

| Freq (GHz) | Received Power Levels (dBm) Mean | Max | Min | Max-to-Mean Ratio | Std Dev (dB) | Normalized Std Dev | Reduced Chi Sq (CL %) | Dmax (<0.0813) | Relative Dmax | Normalized Dsum |
|---|---|---|---|---|---|---|---|---|---|---|
| 1  | 18.4 | 25.0 | −1.5  | 6.6  | 18.3 | 0.98 | 0.436 | 0.0304 | 0.37 | 0.0119 |
| 2  | 14.5 | 22.1 | −13.7 | 7.6  | 14.4 | 0.98 | 0.733 | 0.0342 | 0.42 | 0.0101 |
| 3  | 11.6 | 18.6 | −8.7  | 7.0  | 11.3 | 0.93 | 0.400 | 0.0417 | 0.51 | 0.0202 |
| 4  | 9.9  | 18.3 | −11.5 | 8.4  | 10.1 | 1.05 | 0.473 | 0.0539 | 0.66 | 0.0170 |
| 5  | 7.7  | 15.3 | −21.6 | 7.6  | 7.7  | 1.00 | 1.143 | 0.0454 | 0.56 | 0.0144 |
| 6  | 5.7  | 13.6 | −33.2 | 7.9  | 5.7  | 1.00 | 2.868 | 0.0408 | 0.50 | 0.0138 |
| 7  | 4.2  | 12.1 | −15.4 | 7.9  | 4.4  | 1.05 | 0.737 | 0.0420 | 0.52 | 0.0152 |
| 8  | 3.4  | 9.8  | −24.2 | 6.4  | 2.9  | 0.89 | 0.709 | 0.0634 | 0.78 | 0.0241 |
| 9  | 2.1  | 9.9  | −24.4 | 7.8  | 1.8  | 0.93 | 0.748 | 0.0362 | 0.45 | 0.0132 |
| 10 | 0.7  | 7.9  | −31.9 | 7.2  | 0.8  | 1.02 | 1.159 | 0.0369 | 0.45 | 0.0132 |
| 11 | −0.3 | 8.5  | −29.4 | 8.8  | −0.1 | 1.05 | 0.812 | 0.0294 | 0.36 | 0.0091 |
| 12 | −1.4 | 6.2  | −29.5 | 7.6  | −1.5 | 0.98 | 0.627 | 0.0370 | 0.46 | 0.0120 |
| 13 | −2.5 | 4.4  | −22.9 | 6.9  | −2.6 | 0.98 | 0.555 | 0.0463 | 0.57 | 0.0150 |
| 14 | −2.6 | 4.9  | −30.0 | 7.5  | −2.5 | 1.02 | 0.778 | 0.0461 | 0.57 | 0.0143 |
| 15 | −2.8 | 5.2  | −29.3 | 8.0  | −2.8 | 1.00 | 0.661 | 0.0388 | 0.48 | 0.0153 |
| 16 | −4.5 | 5.3  | −21.2 | 9.8  | −4.0 | 1.12 | 1.122 | 0.0563 | 0.69 | 0.0197 |
| 17 | −5.0 | 2.9  | −29.9 | 7.9  | −4.7 | 1.07 | 0.210 | 0.0350 | 0.43 | 0.0103 |
| 18 | −6.2 | 1.6  | −32.1 | 7.8  | −6.2 | 1.00 | 1.000 | 0.0455 | 0.56 | 0.0107 |

TABLE 2

MS measurement statistics at position 2.

| Freq (GHz) | Received Power Levels (dBm) Mean | Max | Min | Max-to-Mean Ratio | Std Dev (dB) | Normalized Std Dev | Reduced Chi Sq (CL %) | Dmax (<0.0813) | Relative Dmax | Normalized Dsum |
|---|---|---|---|---|---|---|---|---|---|---|
| 1  | 18.5 | 24.2 | −6.9  | 5.7  | 17.9 | 0.87 | 0.880 | 0.0964 | 1.19 | 0.0306 |
| 2  | 14.4 | 20.6 | −7.3  | 6.2  | 13.8 | 0.87 | 0.605 | 0.0548 | 0.67 | 0.0191 |
| 3  | 12.1 | 19.4 | −9.8  | 7.3  | 12.2 | 1.02 | 0.427 | 0.0452 | 0.56 | 0.0116 |
| 4  | 10.1 | 18.1 | −8.7  | 8.0  | 10.2 | 1.02 | 0.974 | 0.0577 | 0.71 | 0.0128 |
| 5  | 7.7  | 15.0 | −12.5 | 7.3  | 7.5  | 0.95 | 0.364 | 0.0348 | 0.43 | 0.0094 |
| 6  | 6.6  | 14.3 | −17.4 | 7.7  | 6.5  | 0.98 | 0.702 | 0.0442 | 0.54 | 0.0151 |
| 7  | 4.8  | 13.6 | −24.1 | 8.8  | 5.0  | 1.05 | 1.200 | 0.0684 | 0.84 | 0.0192 |
| 8  | 2.9  | 11.5 | −19.1 | 8.6  | 2.7  | 0.95 | 0.691 | 0.0485 | 0.60 | 0.0157 |
| 9  | 2.3  | 8.5  | −14.0 | 6.2  | 1.8  | 0.89 | 1.120 | 0.0593 | 0.73 | 0.0244 |
| 10 | 1.0  | 8.5  | −17.3 | 7.5  | 0.9  | 0.98 | 0.551 | 0.0437 | 0.54 | 0.0162 |
| 11 | −0.8 | 8.3  | −29.5 | 9.1  | −0.4 | 1.10 | 1.222 | 0.0404 | 0.50 | 0.0134 |
| 12 | −1.8 | 8.3  | −24.1 | 10.1 | −1.7 | 1.02 | 0.902 | 0.0489 | 0.60 | 0.0237 |
| 13 | −2.4 | 5.4  | −28.0 | 7.8  | −2.3 | 1.02 | 1.095 | 0.0338 | 0.42 | 0.0136 |
| 14 | −2.5 | 5.2  | −30.0 | 7.7  | −2.8 | 0.93 | 0.625 | 0.0325 | 0.40 | 0.0118 |
| 15 | −2.8 | 5.7  | −24.0 | 8.5  | −2.6 | 1.05 | 0.710 | 0.0494 | 0.61 | 0.0131 |
| 16 | −4.4 | 1.6  | −21.9 | 6.0  | −4.7 | 0.93 | 0.447 | 0.0379 | 0.47 | 0.0110 |
| 17 | −5.4 | 2.4  | −31.5 | 7.8  | −5.3 | 1.02 | 1.401 | 0.0604 | 0.74 | 0.0204 |
| 18 | −5.7 | 2.5  | −36.2 | 8.2  | −5.6 | 1.02 | 0.697 | 0.0355 | 0.44 | 0.0124 |

TABLE 3

MS measurement statistics at position 3.

| Freq (GHz) | Received Power Levels (dBm) Mean | Max | Min | Max-to-Mean Ratio | Std Dev (dB) | Normalized Std Dev | Reduced Chi Sq (CL %) | Dmax (<0.0813) | Relative Dmax | Normalized Dsum |
|---|---|---|---|---|---|---|---|---|---|---|
| 1 | 19.5 | 25.8 | −7.7  | 6.3 | 18.9 | 0.87 | 1.019 | 0.0557 | 0.69 | 0.0215 |
| 2 | 14.9 | 22.8 | −12.0 | 7.9 | 14.8 | 0.98 | 0.569 | 0.0374 | 0.46 | 0.0132 |
| 3 | 12.7 | 21.3 | −13.7 | 8.6 | 12.5 | 0.95 | 0.876 | 0.0277 | 0.34 | 0.0128 |
| 4 | 9.5  | 17.0 | −7.8  | 7.5 | 9.5  | 1.00 | 0.859 | 0.0348 | 0.43 | 0.0117 |
| 5 | 7.5  | 15.3 | −16.6 | 7.8 | 7.5  | 1.00 | 0.463 | 0.0276 | 0.34 | 0.0090 |
| 6 | 5.5  | 11.9 | −23.5 | 6.4 | 5.2  | 0.93 | 1.337 | 0.0383 | 0.47 | 0.0083 |
| 7 | 4.3  | 11.3 | −17.4 | 7.0 | 4.4  | 1.02 | 0.584 | 0.0376 | 0.46 | 0.0102 |

TABLE 3-continued

MS measurement statistics at position 3.

| Freq (GHz) | Received Power Levels (dBm) | | | Max-to-Mean Ratio | Std Dev (dB) | Normalized Std Dev | Reduced Chi Sq (CL %) | Dmax (<0.0813) | Relative Dmax | Normalized Dsum |
|---|---|---|---|---|---|---|---|---|---|---|
| | Mean | Max | Min | | | | | | | |
| 8  |  3.1 | 13.4 | −16.5 | 10.3 |  3.9 | 1.20 | 0.783 | 0.0531 | 0.65 | 0.0211 |
| 9  |  1.9 | 10.5 | −22.3 |  8.6 |  2.1 | 1.05 | 0.667 | 0.0503 | 0.62 | 0.0121 |
| 10 |  0.2 |  7.0 | −22.7 |  6.8 |  0.2 | 1.00 | 0.938 | 0.0479 | 0.59 | 0.0138 |
| 11 | −0.3 |  7.0 | −32.6 |  7.3 | −0.4 | 0.98 | 1.097 | 0.0343 | 0.42 | 0.0123 |
| 12 | −1.4 |  6.3 | −29.6 |  7.7 | −1.2 | 1.05 | 0.922 | 0.0572 | 0.70 | 0.0238 |
| 13 | −2.3 |  5.2 | −24.5 |  7.5 | −2.5 | 0.95 | 1.184 | 0.0456 | 0.56 | 0.0141 |
| 14 | −2.1 |  5.4 | −22.3 |  7.5 | −2.3 | 0.95 | 0.702 | 0.0472 | 0.58 | 0.0142 |
| 15 | −3.8 |  5.4 | −34.5 |  9.2 | −3.3 | 1.12 | 1.437 | 0.0586 | 0.72 | 0.0194 |
| 16 | −4.6 |  2.5 | −27.4 |  7.1 | −4.7 | 0.98 | 0.510 | 0.0542 | 0.67 | 0.0174 |
| 17 | −5.1 |  4.2 | −27.4 |  9.3 | −4.7 | 1.10 | 1.199 | 0.0672 | 0.83 | 0.0186 |
| 18 | −5.8 |  3.1 | −33.3 |  8.9 | −5.4 | 1.10 | 0.541 | 0.0464 | 0.57 | 0.0118 |

TABLE 4

DFS measurement statistics at position 1.

| Freq (GHz) | Received Power Levels (dBm) | | | Max-to-Mean Ratio | Std Dev (dB) | Normalized Std Dev | Reduced Chi Sq (CL %) | Dmax (<0.1252) | Relative Dmax | Normalized Dsum |
|---|---|---|---|---|---|---|---|---|---|---|
| | Mean | Max | Min | | | | | | | |
| 1  | 19.2 | 25.3 |  −1.4 | 6.1 | 18.7 | 0.89 | 0.270 | 0.0522 | 0.42 | 0.0178 |
| 2  | 15.2 | 21.6 |   0.0 | 6.4 | 14.5 | 0.85 | 0.669 | 0.1132 | 0.90 | 0.0353 |
| 3  | 12.4 | 19.8 | −10.8 | 7.4 | 12.3 | 0.98 | 0.545 | 0.0603 | 0.48 | 0.0131 |
| 4  |  9.6 | 16.6 | −19.1 | 7.0 |  9.6 | 1.00 | 1.131 | 0.0674 | 0.54 | 0.0259 |
| 5  |  7.6 | 14.3 | −11.9 | 6.7 |  7.7 | 1.02 | 0.460 | 0.0632 | 0.50 | 0.0141 |
| 6  |  6.4 | 14.7 | −12.7 | 8.3 |  6.9 | 1.12 | 0.279 | 0.0665 | 0.53 | 0.0198 |
| 7  |  4.3 | 10.0 | −19.2 | 5.7 |  3.6 | 0.85 | 0.453 | 0.0685 | 0.55 | 0.0253 |
| 8  |  3.3 | 10.4 | −18.9 | 7.1 |  3.6 | 1.07 | 0.772 | 0.0598 | 0.48 | 0.0161 |
| 9  |  2.5 | 10.1 | −21.0 | 7.6 |  2.6 | 1.02 | 0.971 | 0.0561 | 0.45 | 0.0168 |
| 10 |  1.1 |  7.6 | −21.6 | 6.5 |  1.2 | 1.02 | 0.396 | 0.0439 | 0.35 | 0.0102 |
| 11 |  0.7 |  6.1 | −28.4 | 5.4 |  0.2 | 0.89 | 1.661 | 0.0602 | 0.48 | 0.0184 |
| 12 | −2.4 |  5.7 | −54.1 | 8.1 | −2.3 | 1.02 | 0.511 | 0.0607 | 0.48 | 0.0164 |
| 13 | −2.0 |  4.2 | −25.9 | 6.2 | −2.5 | 0.89 | 0.551 | 0.0574 | 0.46 | 0.0189 |
| 14 | −3.1 |  4.3 | −36.4 | 7.4 | −2.8 | 1.07 | 3.138 | 0.0633 | 0.51 | 0.0185 |
| 15 | −3.0 |  2.9 | −19.1 | 5.9 | −3.6 | 0.87 | 0.507 | 0.0735 | 0.59 | 0.0202 |
| 16 | −3.7 |  3.8 | −25.1 | 7.5 | −3.7 | 1.00 | 0.712 | 0.0392 | 0.31 | 0.0106 |
| 17 | −4.6 |  2.2 | −32.4 | 6.8 | −4.8 | 0.95 | 2.533 | 0.0681 | 0.54 | 0.0229 |
| 18 | −5.4 |  1.1 | −26.3 | 6.5 | −5.8 | 0.91 | 0.640 | 0.0835 | 0.67 | 0.0213 |

TABLE 5

DFS measurement statistics at position 2.

| Freq (GHz) | Received Power Levels (dBm) | | | Max-to-Mean Ratio | Std Dev (dB) | Normalized Std Dev | Reduced Chi Sq (CL %) | Dmax (<0.1252) | Relative Dmax | Normalized Dsum |
|---|---|---|---|---|---|---|---|---|---|---|
| | Mean | Max | Min | | | | | | | |
| 1  | 19.7 | 26.8 |  −2.7 | 7.1 | 19.8 | 1.02 | 0.441 | 0.0459 | 0.37 | 0.0154 |
| 2  | 14.6 | 22.1 |  −5.2 | 7.5 | 14.8 | 1.05 | 0.611 | 0.0681 | 0.54 | 0.0196 |
| 3  | 12.7 | 19.4 |  −9.7 | 6.7 | 12.4 | 0.93 | 0.505 | 0.0458 | 0.37 | 0.0146 |
| 4  |  9.7 | 17.0 | −14.1 | 7.3 |  9.7 | 1.00 | 0.699 | 0.0487 | 0.39 | 0.0174 |
| 5  |  7.2 | 13.9 |  −6.6 | 6.7 |  7.0 | 0.95 | 0.690 | 0.1098 | 0.88 | 0.0318 |
| 6  |  6.4 | 15.4 | −17.4 | 9.0 |  7.2 | 1.20 | 0.730 | 0.0791 | 0.63 | 0.0255 |
| 7  |  4.5 | 11.7 | −16.1 | 7.2 |  4.5 | 1.00 | 0.344 | 0.0640 | 0.51 | 0.0139 |
| 8  |  3.7 | 11.9 | −19.5 | 8.2 |  4.0 | 1.07 | 0.875 | 0.0481 | 0.38 | 0.0141 |
| 9  |  1.8 |  9.2 | −23.6 | 7.4 |  1.8 | 1.00 | 0.882 | 0.0515 | 0.41 | 0.0167 |
| 10 |  1.2 |  7.6 | −20.4 | 6.4 |  0.9 | 0.93 | 0.379 | 0.0434 | 0.35 | 0.0154 |
| 11 | −0.2 |  6.4 | −23.5 | 6.6 | −0.6 | 0.91 | 0.582 | 0.0548 | 0.44 | 0.0168 |
| 12 | −1.6 |  7.4 | −19.3 | 9.0 | −0.6 | 1.26 | 1.740 | 0.0874 | 0.70 | 0.0314 |
| 13 | −3.6 |  3.5 | −19.9 | 7.1 | −3.6 | 1.00 | 0.311 | 0.0506 | 0.40 | 0.0128 |
| 14 | −3.0 |  5.2 | −21.4 | 8.2 | −3.0 | 1.00 | 0.241 | 0.0391 | 0.31 | 0.0119 |
| 15 | −3.2 |  3.9 | −21.5 | 7.1 | −3.5 | 0.93 | 0.366 | 0.0562 | 0.45 | 0.0168 |
| 16 | −3.8 |  3.9 | −22.3 | 7.7 | −3.5 | 1.07 | 0.405 | 0.0563 | 0.45 | 0.0161 |
| 17 | −5.6 |  2.1 | −27.1 | 7.7 | −5.2 | 1.10 | 0.863 | 0.0725 | 0.58 | 0.0312 |
| 18 | −5.4 |  1.2 | −23.2 | 6.6 | −5.8 | 0.91 | 0.636 | 0.0601 | 0.48 | 0.0205 |

TABLE 6

DFS measurement statistics at position 3.

| Freq | Received Power Levels (dBm) | | | Max-to-Mean Ratio | Std Dev (dB) | Normalized Std Dev | Reduced Chi Sq (CL %) | Dmax (<0.1252) | Relative Dmax | Normalized Dsum |
|---|---|---|---|---|---|---|---|---|---|---|
| (GHz) | Mean | Max | Min | | | | | | | |
| 1 | 19.4 | 26.4 | −2.8 | 7.0 | 19.7 | 1.07 | 0.888 | 0.581 | 0.46 | 0.0177 |
| 2 | 13.9 | 19.7 | −6.1 | 5.8 | 13.1 | 0.63 | 0.576 | 0.1240 | 0.99 | 0.0467 |
| 3 | 13.1 | 20.4 | −5.2 | 7.3 | 13.3 | 1.05 | 0.448 | 0.0399 | 0.32 | 0.0100 |
| 4 | 9.9 | 17.1 | −5.9 | 7.2 | 10.0 | 1.02 | 0.476 | 0.0605 | 0.48 | 0.0175 |
| 5 | 7.3 | 13.4 | −16.8 | 6.1 | 6.5 | 0.83 | 0.700 | 0.1051 | 0.84 | 0.0319 |
| 6 | 6.4 | 12.6 | −14.7 | 6.2 | 5.9 | 0.89 | 0.623 | 0.0706 | 0.56 | 0.0173 |
| 7 | 4.4 | 12.2 | −26.2 | 7.8 | 4.4 | 1.00 | 1.198 | 0.0525 | 0.42 | 0.0124 |
| 8 | 3.0 | 10.6 | −24.0 | 7.6 | 3.3 | 1.07 | 1.075 | 0.0974 | 0.78 | 0.0207 |
| 9 | 1.4 | 8.4 | −17.5 | 7.0 | 1.2 | 0.95 | 0.881 | 0.0676 | 0.54 | 0.0208 |
| 10 | 1.0 | 9.6 | −24.6 | 8.6 | 1.3 | 1.07 | 1.101 | 0.0472 | 0.38 | 0.0195 |
| 11 | 0.2 | 7.0 | −19.2 | 6.8 | 0.2 | 1.00 | 0.272 | 0.0548 | 0.44 | 0.0152 |
| 12 | −1.7 | 5.4 | −36.7 | 7.1 | −1.2 | 1.12 | 4.543 | 0.1172 | 0.94 | 0.0396 |
| 13 | −2.0 | 5.1 | −30.1 | 7.1 | −2.3 | 0.93 | 1.412 | 0.0994 | 0.79 | 0.0277 |
| 14 | −2.7 | 4.0 | −22.8 | 6.7 | −3.2 | 0.89 | 0.706 | 0.0929 | 0.74 | 0.0390 |
| 15 | −3.8 | 2.7 | −25.0 | 6.5 | −3.9 | 0.98 | 0.309 | 0.0447 | 0.36 | 0.0129 |
| 16 | −4.1 | 3.7 | −26.8 | 7.8 | −3.4 | 1.17 | 0.861 | 0.0853 | 0.68 | 0.0292 |
| 17 | −6.0 | −0.3 | −27.6 | 5.7 | −6.1 | 0.98 | 1.227 | 0.0796 | 0.64 | 0.0223 |
| 18 | −5.4 | 3.2 | −26.3 | 8.6 | −4.8 | 1.15 | 0.718 | 0.0586 | 0.47 | 0.0180 |

TABLE 7

Breakdown of chi-square confidence levels for MS and DFS data sets.

| | | DFS | MS |
|---|---|---|---|
| % of data sets showing CL of . . . | 99% | 24.1 | 11.1 |
| | 95% | 40.7 | 24.1 |
| | 90% | 50.0 | 31.5 |
| | 70% | 66.7 | 57.4 |
| | 50% | 79.6 | 68.5 | shows good agreement with these values.

The max-to-mean power ratio for the field distribution is generally expected to be in the 7-8 dB range for typical mode stir data sets. More precisely, the expected max-to-mean ratio for any given data set can be estimated from the probability distribution function ($f_N$) for the max-to-mean ratio which is given as:

$$f_N(w) = N[F_x(w)]^{N-1} f_x(w) \quad (14)$$

where N is the number of independent samples in the data set, $f_x$ and $F_x$ are the $\chi^2$ probability and cumulative distribution functions respectively, and w is the maximum of the N independent samples. FIG. 18 shows the $\chi^2$ probability distribution function for the received power along with the probability distribution for the max-to-mean ratio for both MS and DFS data sets. As can be seen from the figure, the max-to-mean probability distribution shifts up and narrows with an increased number of samples (the MS data sets consisted of 225 samples while the DFS data sets consisted of 95 samples). This corresponds to a higher expected max-to-mean value and a higher confidence in that value with a larger number of samples. From FIG. 18, it can be seen that the expected max-to-mean ratio for the MS data was 7.6 dB and the max-to-mean ratio for the DFS data was 6.9 dB. The average max-to-mean value for the MS measurements was 7.8 dB and the average max-to-mean value for the DFS measurements was 7.1 dB, showing good agreement with the expected values from theory. The max-to-mean ratios for all data sets are shown in FIG. 19.

Further evaluations of the data spread show good agreement with theory for both measurement techniques. The standard deviation of the data samples is generally expected to be equal to the mean value. Therefore, the mean normalized standard deviation listed in Tables 1-6 was expected to be 1. FIG. 20 shows the mean normalized standard deviation for all measured data sets. A close examination of this data shows the average mean normalized standard deviation to be 1 for both measurement techniques. Finally, the stirring ratio, or the difference between the maximum and minimum received power levels should be greater than 20 dB for an adequately stirred cavity, which was the case for all data sets.

The chi-square goodness-of-fit test demonstrated good agreement between the measured data for both measurement methods and the expected $\chi^2$ distribution. The reduced chi-square statistic for all data sets is shown in FIG. 21. Although the DFS method produced a couple of larger chi-square statistic values, the DFS method did show better overall agreement to the $\chi^2$ distribution with 50% of the data sets producing confidence levels of 90% or more while only 32% of the MS data sets produced 90% or better confidence levels. Table 7 shows the breakdown of the data sets for various confidence levels, the DFS data sets showing a higher level of agreement at all levels.

As with the chi-square test, the K-S goodness-of-fit test demonstrated good agreement between the measured data for both methods and the expected $\chi^2$ distribution. The K-S test, based on the stated success criteria, was passed in all cases except for one MS data set. As determined by equation (15), the commonly accepted success criteria for the K-S test depends on the number of samples in the data set. Since the number of data samples obtained by the two methods was different, a relative K-S statistic was calculated to make meaningful comparisons between the performance of the two methods. The relative K-S statistic, relative $D_{MAX}$, was determined by normalizing the measured $D_{MAX}$ for each data set by the success criteria for that data set FIG. 22 shows the relative $D_{MAX}$ statistic for all data sets. The average relative $D_{MAX}$ for the MS measurements was 56% (that is 56% of the success criteria) while the average relative $D_{MAX}$ for the DFS measurements was slightly better at 53%.

FIG. 23 illustrates a complete set of measured data for a given DFS test covering 1 to 12 GHz (note that the extracted plot shows data that have been normalized to the average value at 5 GHz).

SUMMARY

In the present invention, the discrete frequency stir (DFS) method is used to adequately perturb (or stir) the electromagnetic field within an electrically large, relatively lossless enclosure/cavity through the excitation of that enclosure/cavity by a short duration, continuous wave, radiated source whose frequency is stepped at small increments across a frequency range of interest, and then measure the resulting field levels at the discrete excitation frequencies so that an accurate assessment of the measured field can be made. The primary assessment of the measured field to be made is the determination of the average field level within the enclosure/cavity for a given frequency or frequency range; however, secondary assessments, such as the determination of the measured distribution of field levels, are also accommodated.

Statistical analysis of the DFS method compared to the prior mechanical stir (MS) method shows good agreement with theory. The statistical analysis validates the use of the DFS technique, and other frequency stir techniques in general, for the performance of mode stir measurements. Based on both the chi-square and K-S goodness-of-fit tests, the DFS technique actually provided slightly better agreement to the theoretical $\chi^2$ distribution across the frequency band and among the three different measurement points than did the MS technique. The DFS technique offers a number of advantages over the commonly used FS and MS measurement methods in that it is faster, simpler, as thorough, and at least as effective in stirring the cavity modes when compared to the other methods. The DFS method is particularly well suited toward various shielding effectiveness and cavity Q measurement scenarios, including on vehicle measurement or measurements made at remote sites, were a simple, compact equipment setup and fast test execution are of considerable importance.

While the invention has been described in connection with the above-described embodiments, it is to be understood that they are merely illustrative of the principles of the invention, and that numerous modifications may be made to the methods and apparatus described without departing from the spirit and scope of the invention as defined by the appended claims.

The invention claimed is:

1. A method of electromagnetic testing of mode stirring type for a given enclosure or cavity, comprising the steps of:
   providing excitation inputs at discrete frequencies stepped in small frequency steps across a frequency range of interest, wherein the small frequency steps are at least slightly larger than a resonant mode bandwidth associated with the given enclosure or cavity in order to provide statistically independent electromagnetic response measurements; and
   measuring electromagnetic response values to the excitation inputs for analysis of an electromagnetic response characteristic of the given enclosure or cavity,
   wherein the excitation inputs are stepped in small frequency steps across a stirring bandwidth selected so as to contain a statistically significant number of electromagnetic response measurement values,
   wherein an average field level at a given frequency is determined by averaging over the electromagnetic response measurement values obtained over the stirring bandwidth when centered on the given frequency, and
   further comprising the step of performing an autocorrelation check of the electromagnetic response measurement values to determine if they have a desired sample independence necessary to perform a statistical analysis on the measured data,
   wherein if the autocorrelation check shows that the resonant mode bandwidth was not correctly selected and the subsequent frequency step size was too small, then measuring electromagnetic response values at a larger frequency step size based on an improved estimate of the resonant mode bandwidth.

2. A method of electromagnetic testing according to claim 1, wherein a statistical evaluation is performed on the electromagnetic response measurement values obtained over the stirring bandwidth.

3. A method of electromagnetic testing according to claim 1, wherein, for a high Q cavity such as a reverberation chamber the frequency step size is selected in the range of 10 KHz to 1 MHz for a frequency range of 100 MHz to 18 GHz.

4. A method of electromagnetic testing according to claim 1 wherein, for a moderate Q cavity such as a commercial aircraft interior, the frequency step size is selected in the range of 200 KHz to 10 MHz for a frequency range of 100 MHz to 18 GHz.

5. A method of electromagnetic testing according to claim 1 wherein the stirring bandwidth is selected to be small enough so that the average field value within the given enclosure or cavity is constant across the stirring bandwidth.

6. A method of electromagnetic testing according to claim 1 wherein the stirring bandwidth is selected to be large enough to contain in the range of about 100 or more electromagnetic response measurement values.

7. A method of electromagnetic testing according to claim 1, wherein the frequency step size is selected to be small enough to maintain a desired frequency resolution in the averaged field values so as not to "average out" resonant effects in the given enclosure or cavity.

8. A method of electromagnetic testing according to claim 1 wherein a precision network analyzer is used to measure a large number of electromagnetic response values in small frequency steps over a large frequency range.

9. A method of electromagnetic testing according to claim 1 using a frequency step size of about 1 MHz within about a 100 MHz stirring bandwidth.

10. A method of electromagnetic testing according to claim 1, used for testing of an aircraft cavity for one of the group consisting of: (a) shielding against radio frequency threats found near an airport; and (2) shielding against radio frequency threats found on board the aircraft.

11. A method of electromagnetic testing according to claim 1, wherein the measuring of electromagnetic response values is performed at a plurality of positions within the given enclosure or cavity.

12. A method of electromagnetic testing of mode stirring type for a given enclosure or cavity, comprising the steps of:
   providing excitation inputs at discrete frequencies stepped in small frequency steps across a frequency range of interest, wherein the small frequency steps are at least slightly larger than a resonant mode bandwidth associated with the given enclosure or cavity in order to provide statistically independent electromagnetic response measurements; and
   measuring electromagnetic response values to the excitation inputs for analysis of an electromagnetic response characteristic of the given enclosure or cavity,
   wherein the excitation inputs are stepped in small frequency steps across a stirring bandwidth selected so as to contain a statistically significant number of electromagnetic response measurement values.

wherein an average field level at a given frequency is determined by averaging over the electromagnetic response measurement values obtained over the stirring bandwidth when centered on the given frequency, and further comprising the step of performing an autocorrelation check of the electromagnetic response measurement values to determine if they have a desired sample independence necessary to perform a statistical analysis on the measured data, wherein if the autocorrelation check shows that the resonant mode bandwidth was not correctly selected, then sifting through the data in order to obtain an uncorrelated data set.

13. A method of electromagnetic testing according to claim 12 wherein the stirring bandwidth is selected to be small enough so that the average field value within the given enclosure or cavity is constant across the stirring bandwidth.

14. A method of electromagnetic testing according to claim 12 wherein the stirring bandwidth is selected to be large enough to contain in the range of about 100 or more electromagnetic response measurement values.

15. A method of electromagnetic testing according to claim 12, wherein the frequency step size is selected to be small enough to maintain a desired frequency resolution in the averaged field values so as not to "average out" resonant effects in the given enclosure or cavity.

16. A method of electromagnetic testing according to claim 12, wherein a precision network analyzer is used to measure a large number of electromagnetic response values in small frequency steps over a large frequency range.

17. A method of electromagnetic testing according to claim 12 used for testing of an aircraft cavity for one of the group consisting of: (a) shielding against radio frequency threats found near an airport; and (2) shielding against radio frequency threats found on board the aircraft.

18. A method of electromagnetic testing according to claim 12 wherein the measuring of electromagnetic response values is performed at a plurality of positions within the given enclosure or cavity.

19. A method of electromagnetic testing according to claim 12, wherein, for a high Q cavity such as a reverberation chamber the frequency. step size is selected in the range of 10 KHz to 1 MHz for a frequency range of 100 MHz to 18 GHz.

20. A method of electromagnetic testing according to claim 12, wherein, for a moderate Q cavity such as a commercial aircraft interior, the frequency step size is selected in the range of 200 KHz to 10 MHz for a frequency range of 100 MHz to 18 GHz.

* * * * *